US011230585B2

(12) United States Patent
Gatos et al.

(10) Patent No.: US 11,230,585 B2
(45) Date of Patent: Jan. 25, 2022

(54) PROINSULIN DERIVATIVES

(71) Applicant: CHEMICAL & BIOPHARMACEUTICAL LABORATORIES OF PATRAS S.A., Patras (GR)

(72) Inventors: Dimitrios Gatos, Patras (GR);
Alexandra Anastasiou, Patras (GR);
Kleomenis Barlos, Patras (GR)

(73) Assignee: CHEMICAL & BIOPHARMACEUTICAL LABORATORIES OF PATRA, Patras (GR)

( * ) Notice: Subject to any disclaimer, the term of this patent is extended or adjusted under 35 U.S.C. 154(b) by 0 days.

(21) Appl. No.: 16/330,154

(22) PCT Filed: Sep. 5, 2017

(86) PCT No.: PCT/IB2017/055336
§ 371 (c)(1),
(2) Date: Mar. 4, 2019

(87) PCT Pub. No.: WO2018/047062
PCT Pub. Date: Mar. 15, 2018

(65) Prior Publication Data
US 2019/0263881 A1   Aug. 29, 2019

(30) Foreign Application Priority Data
Sep. 6, 2016 (GR) .............................. 20160100458

(51) Int. Cl.
| | | |
|---|---|---|
| *A61K 38/28* | (2006.01) | |
| *C07K 14/62* | (2006.01) | |
| *A61P 3/10* | (2006.01) | |
| *A61K 38/00* | (2006.01) | |

(52) U.S. Cl.
CPC ................ *C07K 14/62* (2013.01); *A61P 3/10* (2018.01); *A61K 38/00* (2013.01)

(58) Field of Classification Search
CPC ................................. C07K 14/62; A61K 38/28
See application file for complete search history.

(56) References Cited

U.S. PATENT DOCUMENTS

| | | | |
|---|---|---|---|
| 5,304,473 A | 4/1994 | Belagaje et al. | |
| 5,597,796 A | 1/1997 | Brange et al. | |
| 6,444,641 B1 | 9/2002 | Flora | |
| 8,785,384 B2 * | 7/2014 | Barlos ..................... | A61P 9/00 514/12.1 |
| 10,100,098 B2 * | 10/2018 | Zimmerman ............. | C07K 14/62 |
| 2009/0069216 A1 | 3/2009 | Naver et al. | |
| 2010/0216690 A1 | 8/2010 | Madsen et al. | |

FOREIGN PATENT DOCUMENTS

| | | |
|---|---|---|
| EP | 0195691 A1 | 9/1986 |
| EP | 0427296 A1 | 5/1991 |
| EP | 0518587 A2 | 12/1992 |
| EP | 0741188 A2 | 11/1996 |
| EP | 1193272 A1 | 4/2002 |
| WO | 9620724 A1 | 7/1996 |
| WO | 9921573 A1 | 5/1999 |
| WO | 9964574 A1 | 12/1999 |
| WO | 2002/079251 A2 | 10/2002 |
| WO | 2005054291 A1 | 6/2005 |
| WO | 2007096332 A1 | 8/2007 |
| WO | 2007104738 A2 | 9/2007 |
| WO | 2011042762 A2 | 4/2011 |
| WO | 2015083114 A2 | 6/2015 |

OTHER PUBLICATIONS

Berge et al., (1977) "Pharmaceutical Salts," Journal of Pharmaceutical Sciences, 66(1):21 pages.
Gennaro, A. (1985) Remington's Pharmaceutical Sciences, 17th Edition, 9 pages.
Horwell, D. (1995) "The 'peptoid' approach to the design of non-peptide, small molecule agonists and antagonists of neuropeptides," Trends Biotechnol., 13(4):132-134.
Simon et al., (1992) "Peptoids: A modular approach to drug discovery," Proc. Natl. Acad. Sci. USA, 89:9367-9371.
Sohma et al., (2009) "Biomimetic synthesis of lispro insulin via a Chemically synthesized "mini-proinsulin" prepared by oxime-forming ligation," J. Am. Chem. Soc., 131:16313-16318.
Tofteng et al., (2008) "Total synthesis of desB30 insulin analogues by biomimetic folding of single-chain precursors," ChemBioChem, 9:2989-2996.

(Continued)

*Primary Examiner* — Gyan Chandra
(74) *Attorney, Agent, or Firm* — Lathrop GPM LLP; Brian C. Trinque

(57) ABSTRACT

A first aspect of the invention relates to a polypeptide compound of formula (I):

A-C-B        (I)

wherein:
  A is the A chain of insulin or a functional derivative or variant thereof;
  B is the B chain of insulin or a functional derivative or variant thereof;
  C is a peptide of the formula:

$(X_1)_p\text{-}(X_2)_n\text{-}(X_3)_q$ wherein:
  each $X_1$ and $X_3$ is independently a basic amino acid;
  each $X_2$ is independently a natural or unnatural amino acid;
  p is 1 or 2;
  q is 0, 1 or 2;
  n is 0, 1, 2 or 3.

Further aspects of the invention relate to pharmaceutical compositions comprising said polypeptide compound, and therapeutic uses thereof. Another aspect relates to the use of said polypeptide compounds in the preparation of insulin and derivatives thereof.

20 Claims, 4 Drawing Sheets

Specification includes a Sequence Listing.

(56) References Cited

OTHER PUBLICATIONS

Wade et al. (1994) Handbook of Pharmaceutical Excipients, Second Edition.
Heath, W. F. et al., "(A-C-B) Human Proinsulin, a Novel Insulin Agonist and Intermediate in the Synthesis of Biosynthetic Human Insulin", Journal of Biological Chemistry, Jan. 5, 1992 American Society for Biochemistry and Molecular Biology, US—ISSN 0021-9258; vol. 267, No. 1, pp. 419-425, Jan. 5, 1992, XP003018538.
Rajpal et al., "Single-Chain Insulins as Receptor Agonists", Molecular Endocrinology, May 1, 2009 Endocrine Society—ISSN 0888-8809; DOI: 10.1210/me.2008-0349, vol. 23, No. 5, pp. 679-688, May 1, 2009, XP055085086.
Wetzel et al., "Expression in *Escherichia coli* of a chemically synthesized gene for a 'mini-c' analog of human proinsulin", Gene, Dec. 1, 1981, Elsevier, Amsterdam, NL—ISSN 0378-1119, DOI: 10.1016/0378-1119(81)90061-5, vol. 16, No. 1-3, pp. 63-71, Dec. 1, 1981, XP023790906.
Thim et al., "Secretion and processing of insulin precursors in yeast", Proceedings of the National Academy of Sciences of the United States of America, Sep. 1, 1986 National Academy of Sciences, US—ISSN 0027-8424, DOI: 10.1073/pnas.83.18.6766, vol. 83, No. 18, pp. 6766-6770, Sep. 1, 1986, XP002100937.
Gatos et al., "An Efficient Strategy for the Synthesis of Insulin Derivatives Via "Inverted" Mini-Proinsulin Precursors", Journal of Peptide Science, Sep. 4, 2016 & 34th European Peptide Symposium; Leipzig, Germany, vol. 22, No. Suppl. S2, p. S61, Dec. 10, 2016, XP002775163.
Belgi et al., "The chemical synthesis of insulin: From the past to the present", Immunology, Endocrine and Metabolic Agents in Medicinal Chemi, Jan. 1, 2011 Bentham Science Publishers Ltd., NL—ISSN 1871-5222, DOI: 10.2174/187152211794519412, vol. 11, No. 1, pp. 40-47, Jan. 1, 2011, XP008164062.
Fa Liu et al., "Concise Synthetic Routes to Human Insulin", Organic Letters, 14 (23), 6012-6015 CODEN: ORLEF7; American Chemical Society, US—ISSN 1523-7060; DOI: 10.1021/01400149j, vol. 15, No. 4, pp. 960-963, Feb. 7, 2013, XP055419919.
International Search Report dated Nov. 17, 2017 in International Application No. PCT/IB2017/055336.
Qiao, Zhi-Song et al., "In Vitro Refolding of Human Proinsulin", Journal of Biological Chemistry, 2003, vol. 278, No. 20, pp. 17800-17809.
Min, Chen-Yin et al., "Unfolding of Human Proinsulin", Eur J. Biochem., 2004, vol. 271, pp. 1737-1747.
Weiss M A, "Proinsulin and the Genetics of Diabetes Mellitus", Journal of Biological Chemistry, Jul. 17, 2009, vol. 284, No. 29, pp. 19159-19163.
Fa Liu et al., "Chemical Synthesis of Peptides Within The Insulin Superfamily", Journal of Peptide Science, Feb. 22, 2016, vol. 22, No. 5, pp. 260-270 XP055355233.

\* cited by examiner

PROINSULIN DERIVATIVES

RELATED APPLICATIONS

This application is a 35 U.S.C. § 371 filing of International Application No. PCT/62017/055336, filed Sep. 5, 2017, which claims the benefit of Greece Patent Application No. 20160100458, filed Sep. 6, 2016. The entire contents of these applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Mar. 1, 2019, is named DYT-025US-30847429_1.txt and is 10,259 bytes in size.

The present invention relates to proinsulin derivatives, more specifically inverted proinsulin derivatives, that have applications in the preparation of insulin. The proinsulin derivatives of the invention also have potential applications as therapeutic moieties in their own right.

BACKGROUND TO THE INVENTION

Insulin and its derivatives are the most important drugs for the treatment of diabetes, with annual sales of over 20 billion and with a steadily increasing market.

Insulin is a peptide hormone secreted by the β-cells of the pancreas. It consists of two peptide chains, A and B, which are linked by two intermolecular disulphide bonds. The A-chain also contains an additional intramolecular disulfide bond. Human insulin has the structure 2.

A-chain

Gly-Ile-Val-Glu-Gln-Cys-Cys-Thr-Ser-Ile-Cys-Ser-Leu-Tyr-Gln-Leu-Glu-Asn-Tyr-Cys-Asn

Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys-Thr

B-Chain

Structure 2 = human Insulin

Insulins are typically manufactured on a large scale (hundreds of kg) starting from proinsulins which are recombinantly produced. Subsequently proinsulin is folded and the connecting C-peptide is removed enzymatically using trypsin and carboxypeptidase B to yield the mature insulin peptide.

More specifically, insulin is produced as a single-chain precursor, preproinsulin, which consists of a propeptide of 24 amino acid followed by proinsulin containing 86 amino acids. The sequence of the prepropeptide is Prepeptide-[B-chain]-Arg-Arg-[connecting peptide]- Lys-Arg-[A-chain], wherein the connecting peptide consists of 31 amino acids. After the enzymatic removal of the prepeptide, the three disulfide bonds are formed and proinsulin is produced.

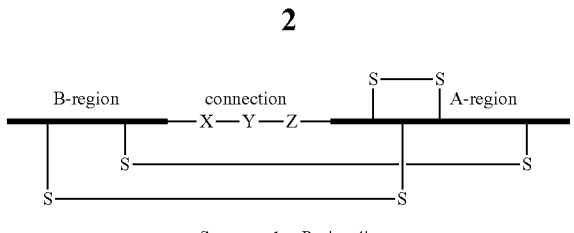

Structure 1 = Proinsulin

The mature insulin is then liberated by enzymatic cleavage of the connecting peptide at the Arg-Arg and Lys-Arg sites.

Proinsulin has a 100-fold lower affinity for the insulin receptor than native insulin because the essential residues for binding to the receptor, namely the N-terminal amino function of the A-chain and the C-terminal carboxyl function of the B-chain, are blocked. The stability and solubility properties of insulin are important in the context of insulin therapeutics. A number of insulin analogues are known in the art. By way of example, single-chain insulin analogues with insulin activity are disclosed in EP1193272. These single-chain insulins have a modified C-peptide of 5-18 amino acids and are reported to have up to 42% insulin activity.

U.S. Pat. No. 5,597,796 discloses insulin analogues in which two or more amino acid residues are substituted by Glu and/or Asp. Similarly, US 20090069216 and WO 2007/096332 disclose fast acting single chain insulins containing a modified B-chain and a connecting peptide. The resulting analogues are particularly well suited for transdermal administration. Fibrillation-resistant insulin and insulin analogues are disclosed in U.S. Pat. No. 8,192,957. Pegylated single chain insulins are disclosed in US 2010/0216690, whereas acylated single chain insulins are disclosed in WO 2007/104738.

WO 2005/054291 discloses single chain insulin analogues wherein the A-chain and B-chains are connected by a connecting peptide of 5-11 amino acids. Likewise, WO 95/16708 also discloses single chain insulin analogues wherein the A-chain and B-chains are connected by a connecting peptide of 1-15 amino acids, in which the C-terminal amino acid residue is other than Lys or Arg. EP0427296 discloses human insulin precursors of the general formula B(1-29)-$X_n$-Y-A(1-21), wherein $X_n$ is a peptide chain with n naturally occurring amino acid residues, where n is 0 to 33 and Y is Arg or Lys. Similarly, EP0741188 discloses single chain insulin derivatives of the formula b-BP-a having significant insulin activity, where BP is a bridging peptide of 10 to 14 amino acids; these single chain insulins are reported to have insulin activity but also a high affinity to the IGF-1 receptor. Despite numerous efforts, a chemical and economically feasible route to insulin has not yet been developed. The methods which have been applied to date include the random mixing of the linear A and B chains and their air oxidation, the mixing of the sulfonated A and B-chains, the site-directed building of the three disulfide bonds and the biomimetic folding of single-chain precursors (Sohma, Y. and Kent, S. B. J. Am. Chem. Soc. 2009, 131, 16313-16318; Tofteng, A. P.; Jensen, K. J.; Schaffer, L.; Hoeg-Jensen, T. Chem-BioChem 2008, 9, 2989-2996).

A-C-B 'inverted'-proinsulins with a connecting C-peptide are also known to yield insulin derivatives. By way of example, EP0518587 discloses A-C-B proinsulin derivatives wherein the linker peptide C is a fragment of the formula $X_1$-$X_2$-P-$X_3$-$X_4$, wherein $X_1$ to $X_4$ are basic amino acids and P is peptide from 4 to 35 amino acids which does not contain a cysteine residue (see also W. F. Heath et al, The Journal of Biological Chemistry, Vol. 276, No. 1, p 419-425). It is generally understood that the C-peptide of a natural or inverse proinsulin must be of a minimum length in order to have the required flexibility to fold correctly to the natural mature proinsulin or reverse proinsulin.

The present invention seeks to provide alternative proinsulin derivatives that are useful in the preparation of insulin, and also as therapeutic moieties in their own right. In particular, the invention seeks to provide proinsulin derivatives that give rise to one or more advantages in terms of solubility, activity, yield, purity and/or ease of synthesis.

STATEMENT OF INVENTION

The present invention relates to proinsulin derivatives, more specifically inverted proinsulin derivatives of formula A-C-B.

Thus, a first aspect of the invention relates to a polypeptide compound of formula (I):

A-C-B      (I)

wherein:
A is the A chain of insulin or a functional derivative or variant thereof;
B is the B chain of insulin or a functional derivative or variant thereof;
C is a connecting peptide of the formula:

$(X_1)_p$-$(X_2)_n$-$(X_3)_q$ wherein:
each $X_1$ and $X_3$ is independently a basic amino acid;
each $X_2$ is independently a natural or unnatural amino acid;
p is 1 or 2;
q is 0, 1 or 2;
n is 0, 1, 2 or 3.

The presently claimed inverted proinsulin derivatives differ from those known in the art by virtue of the fact that they contain a shorter connecting peptide (they are "super mini" insulins). Surprisingly, the Applicants have found that C-peptides containing 7 amino acids or less (including those with only a single amino acid such as the inverse proinsulin A-Arg-B) and their corresponding protected or partially protected derivatives are useful proinsulin precursors.

DETAILED DESCRIPTION

Figure 1:
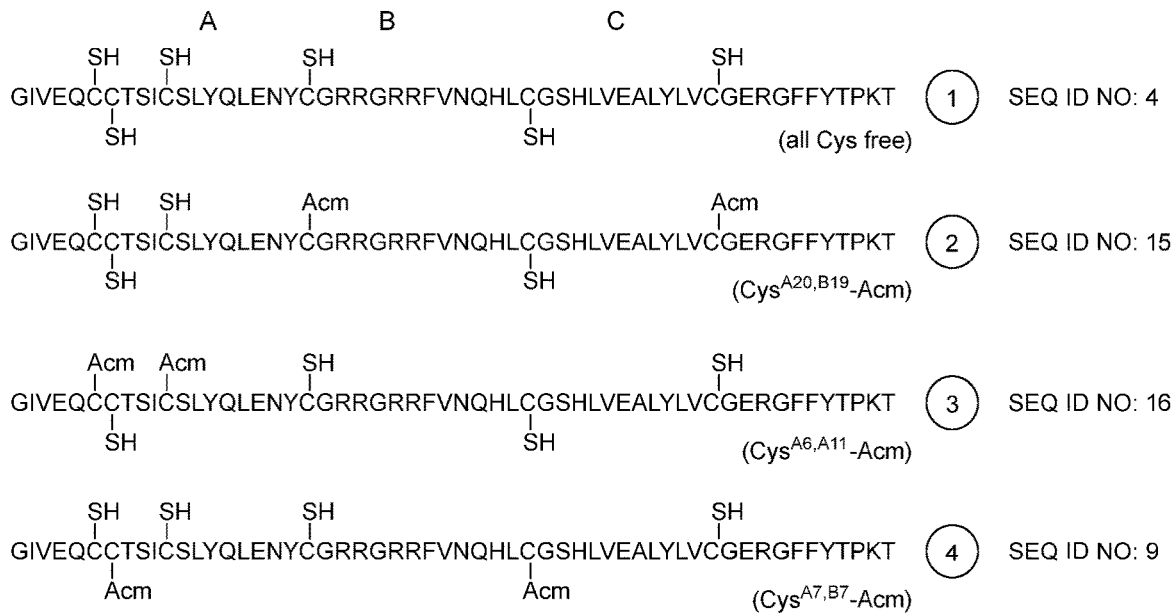
FIG. 1 shows ACB-proinsulin peptides 1-4 according to the invention.
Figure 2:
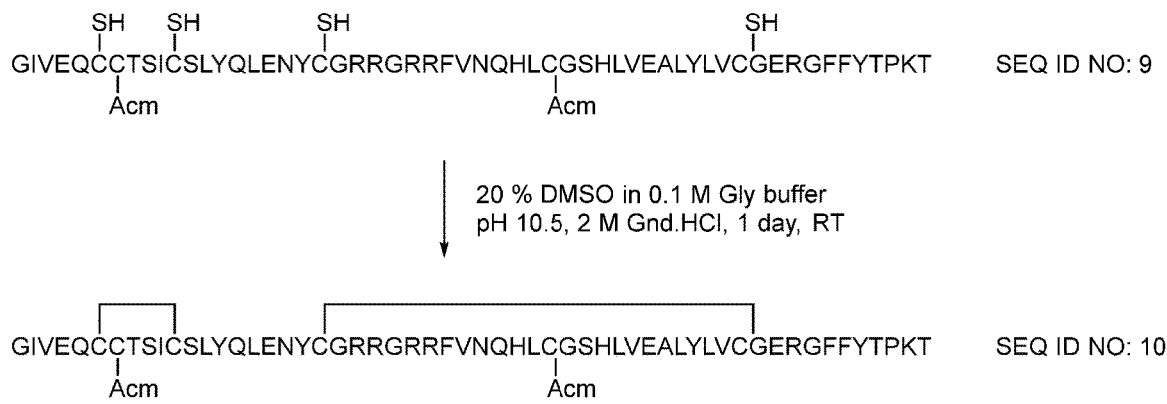
FIG. 2 shows a schematic representation of the first oxidation step (with DMSO) of peptide 4 (C(Acm)$^7$C(Acm)$^{33}$).
Figure 3:
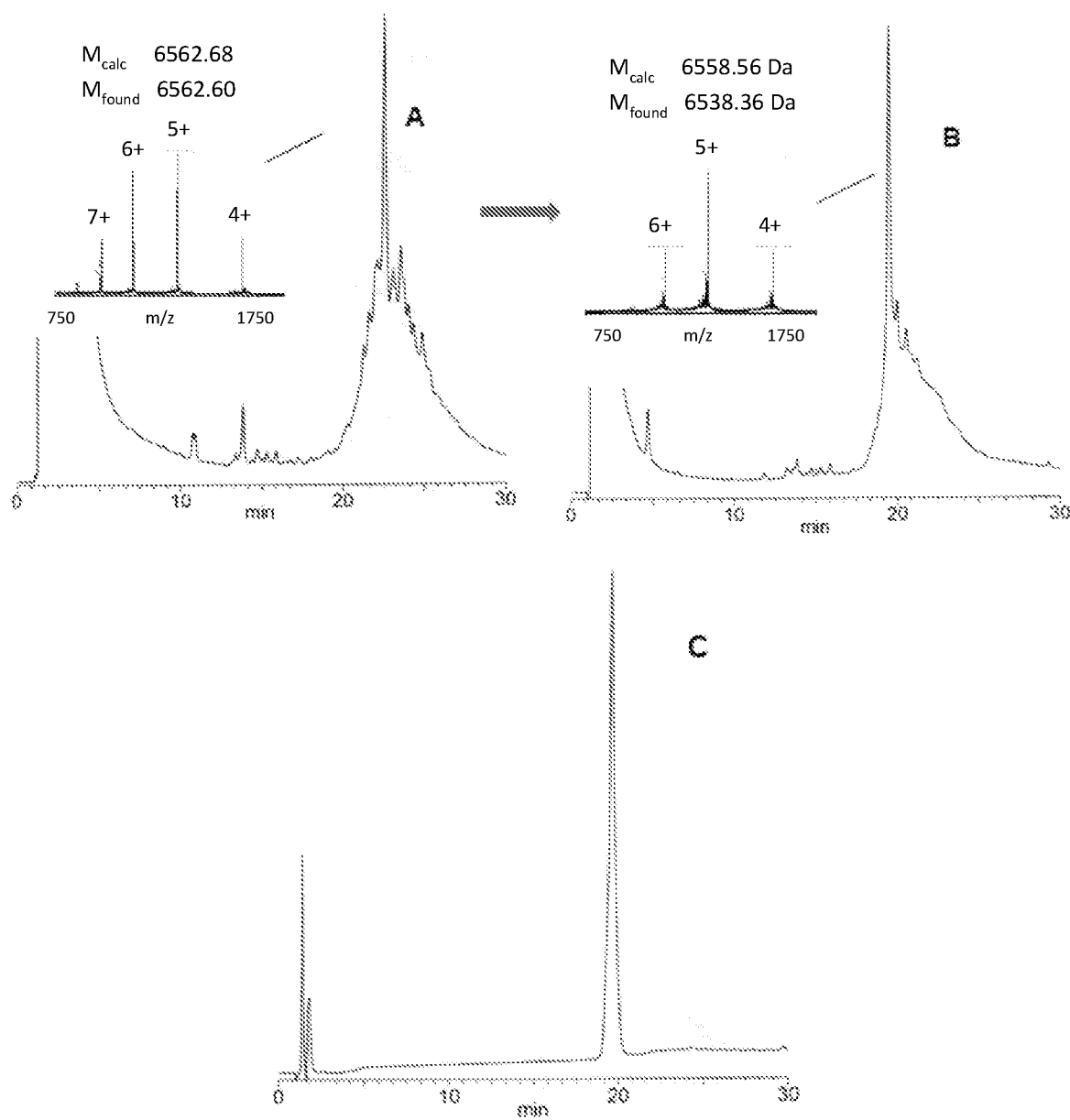
FIG. 3 shows HPLC profiles and ESI-MS of crude reduced C(Acm)$^7$C(Acm)$^{33}$) reverted proinsulin with C=RRGRR (A), the product obtained after its oxidation with DMSO (B), and the HPLC profile of the purified product (bis-oxidized ACB-proinsulin with C=RRGRR) (C).
Figure 4:
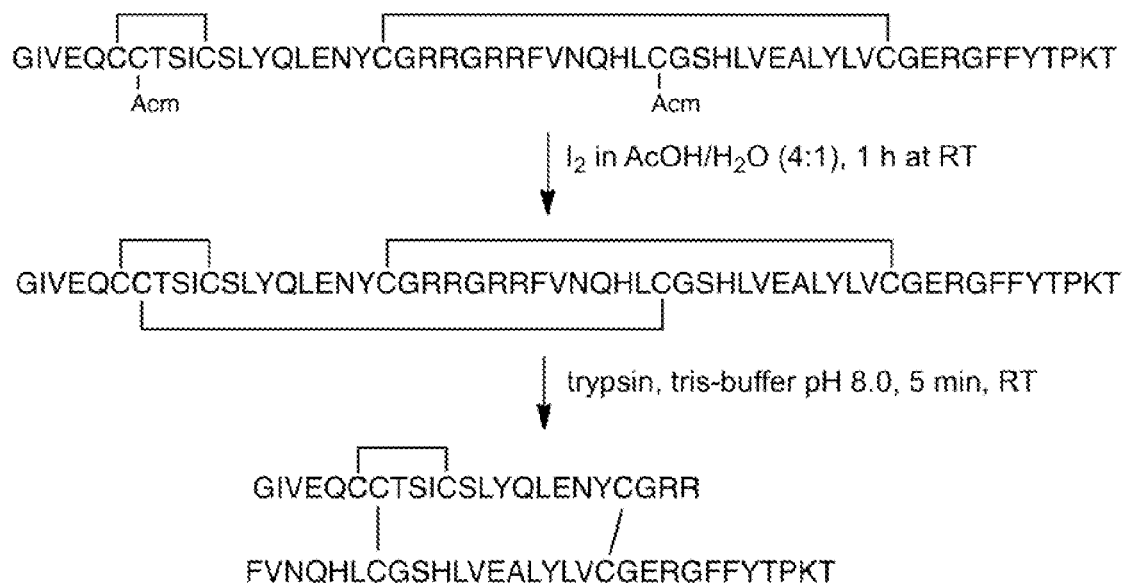
FIG. 4 shows a schematic representation of the second oxidation step (with $I_2$) of peptide 4 (C(Acm)$^7$C(Acm)$^{33}$) reverted proinsulin with C=RRGRR and C-peptide excision by trypsinolysis.
Figure 5:
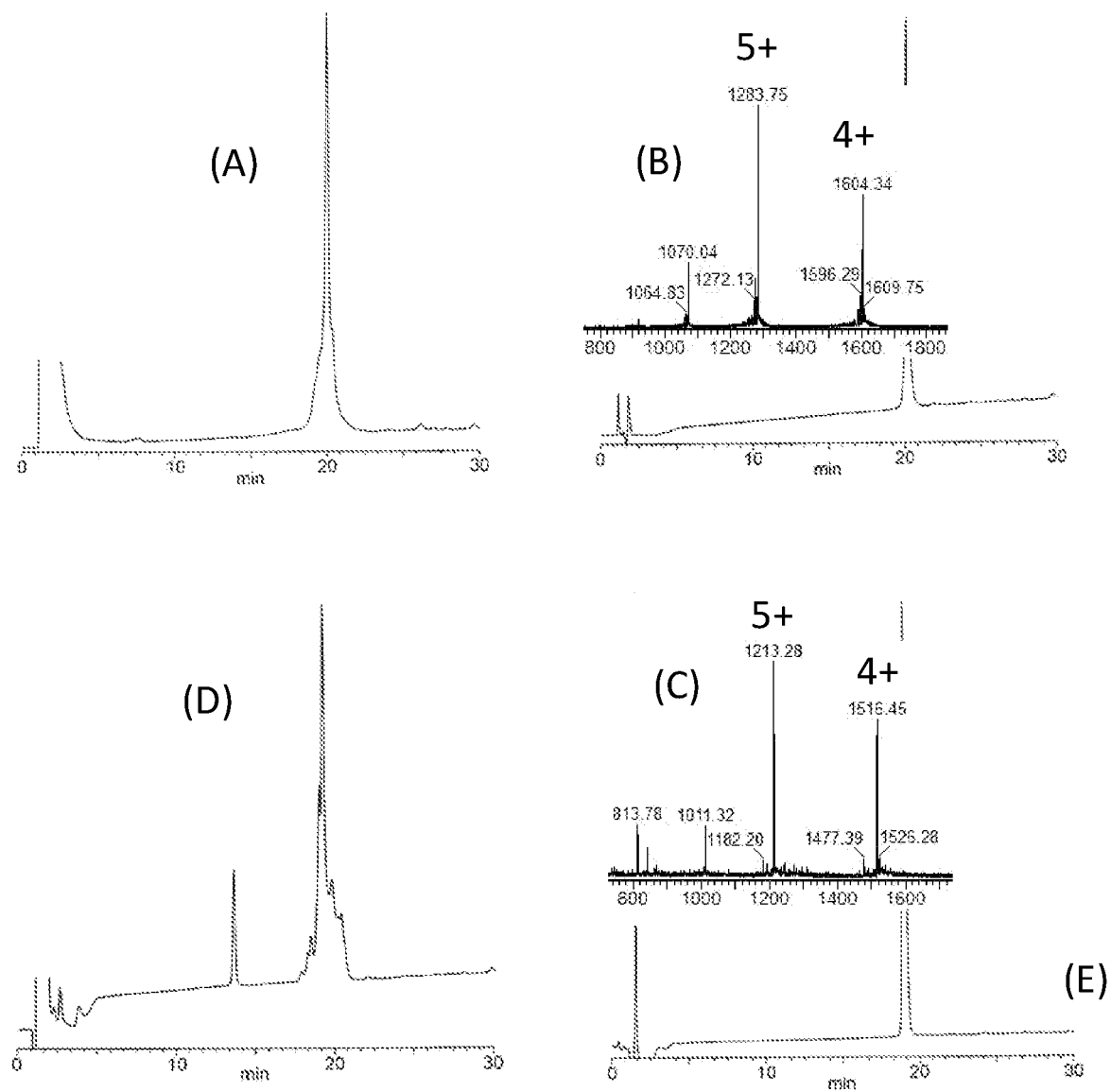
FIG. 5 shows HPLC profiles and corresponding MS-spectra of the crude inverted proinsulin with C-peptide RRGRR (A); the same after purification (B); the product mixture obtained after trypsin cleavage (D) and the final purified [Gly$^{A21}$, Arg$^{A22, A23}$] insulin derivative (E).

The presently claimed peptide compounds were developed with a view to improving the solid phase chemical synthesis of proinsulins.

Ideally, the peptide must not contain problematic peptide synthesis regions, for example, those that give rise to the formation of β-turns and β-sheets during the on resin peptide chain elongation. The presently claimed peptides are inverted proinsulin derivatives in the order A-C-B, rather than the natural B-C-A order. These inverted proinsulin derivatives have been shown to be synthetically easier to prepare than the corresponding B-C-A proinsulins.

Preferably, the inverted proinsulins of the invention comprise residues in the C-peptide (for example, as amino acid $X_2$) which disrupt the formation of β-sheets and β-turns. Suitable residues in this regard include Pro, Hyp and pseudoprolines. Insertion of these residues into the C-peptide allows the effective synthesis of inverse proinsulins.

Preferably, the C peptide contains residues that improve the solubility in solvents used in the purification step. Suitable residues in this regard include Pro, Hyp, basic amino acids such as Arg or Lys, or acidic and hydrophilic amino acids, such as Glu and Ser. To obtain proinsulins of high purity, smaller protected peptides can be condensed in solution or on solid-phase. Preferably, in order to avoid racemisation in the condensation reactions, the C-terminal amino acids of the fragments are typically selected from Gly, Pro, β-Ala and amino acids which contain an oligo or poly-glycol part in their structure, for example the —NH—(CH$_2$CH$_2$O)$_{n'}$—CO— structural element, where n' is an integer, for example 1 to 10, more preferably 1 to 5.

Preferably, to facilitate excision of the C-peptide, one or more basic amino acids are positioned at the C-terminus of the A-chain and the amino terminus of the B-chain, i.e. $(X_1)_p$ where p is 1 or 2, and $(X_3)_q$, where q is 1 or 2.

As used herein, the term "variant" includes any variation wherein (a) one or more amino acid residues are replaced by a naturally or non-naturally occurring amino acid residue (b) the order of two or more amino acid residues is reversed, (c) one, two or three amino acids are deleted, (d) a spacer group is present between any two amino acid residues, (e) one or more amino acid residues are in peptoid form, (f) the (N—C—C) backbone of one or more amino acid residues of the peptide has been modified, (g) one or more additional amino acids are present at the N-terminus and/or the C-terminus, or any of (a)-(g) in combination. Preferably, the variants arise from one of (a), (b) or (c).

More preferably, one to five, or one to four, or one to three amino acids residues are substituted by one or more other amino acid residues. Even more preferably, two amino acid residues are substituted by another amino acid residue. More preferably still, one amino acid residue is substituted by another amino acid residue. Preferably, the substitution is homologous.

Homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine, diaminobutyric acid ornithine, norleucine ornithine, pyridylalanine, thienylalanine, naphthylalanine and phenylglycine, a more detailed list of which appears below. More than one amino acid residue may be modified at a time.

As used herein, amino acids are classified according to the following classes;
  basic; H, K, R
  acidic; D, E
  non-polar; A, F, G, I, L, M, P, V, W
  polar; C, N, Q, S, T, Y,
  (using the internationally accepted single letter amino acid notation) and homologous and non-homologous substitution is defined using these classes. Thus, homologous substitution is used to refer to substitution from within the same class, whereas non-homologous substitution refers to substitution from a different class or by an unnatural amino acid.

Suitable spacer groups that may be inserted between any two amino acid residues of the carrier moiety include alkyl groups such as methyl, ethyl or propyl groups in addition to amino acid spacers such as glycine or β-alanine residues. A further form of variation, type (e), involving the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example, Simon R J et al., PNAS (1992) 89(20), 9367-9371 and Horwell D C, Trends Biotechnol. (1995) 13(4), 132-134. Type (f) modification may occur by methods such as those described in International Application PCT/GB99/01855 (WO 99/64574).

It is preferable for amino acid variation, preferably of type (a) or (b), to occur independently at any position. As mentioned above more than one homologous or non-homologous substitution may occur simultaneously. Further variation may occur by virtue of reversing the sequence of a number of amino acid residues within a sequence.

In one embodiment the replacement amino acid residue is selected from the residues of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

The replacement amino acid residue may additionally be selected from unnatural amino acids as described below.

As used herein, the term "derivative" refers to insulin that has undergone chemical modification, for example, to the amino acid side chains at the N-terminus and/or the C-terminus. Preferably, the chemical modification serves to alter the absorption, distribution, metabolism, and excretion characteristics of the analogue. Semisynthetic insulins were clinically used for some time based on chemical modification of animal insulins, for example Novo Nordisk enzymatically converted porcine insulin into semisynthetic 'human' insulin by removing the single amino acid that varies from the human variety, and chemically adding the human amino acid.

In one preferred embodiment, the insulin is chemically modified to alter its isoelectric point. Normal unmodified insulin is soluble at physiological pH. Modified derivatives of insulin have been created that have a shifted isoelectric point so that they exist in a solubility equilibrium in which most precipitates out but slowly dissolves in the bloodstream and is eventually excreted by the kidneys.

As used herein, the term "functional derivative of insulin" refers to any molecule that performs a similar or equivalent biological function to insulin. The functional derivative may or may not be structurally similar to insulin in terms of its chemical structure.

In one preferred embodiment, the single chain insulin analogue of the invention is derived from animal insulin.

The amino acid sequence of animal insulins in different mammals may be similar to human insulin (insulin human INN). However, there is considerable variability within vertebrate species. Porcine insulin has only a single amino acid variation from the human variety, and bovine insulin varies by three amino acids. Both are active on the human receptor with approximately the same strength. Bovine insulin and porcine insulin were the first clinically used insulin analogues (naturally occurring, produced by extraction from animal pancreas), at the time when biosynthetic human insulin (insulin human rDNA) was not available. Insulin from sharks and some species of fish may be also effective.

In another preferred embodiment, the single chain insulin analogue of the invention is derived from human insulin, or an analogue thereof. More preferably, the insulin is biosynthetic insulin (insulin human rDNA). In one preferred embodiment, the insulin is a derivative selected from Insulin Glargin (Lantus), Insulin Lispro (Humalog), Insulin Detemir (Levemir), Insulin Aspart (novolog), Insulin Degludec and biotinylated insulin.

Other embodiments of this invention include rabbit, monkey, horse, rat I, rat II, porcine, bovine-Iamb, dog, guinea pig, chinchilla, or duck ACB-proinsulin molecules.

In one preferred embodiment, the A chain is the naturally occurring amino acid sequence of the A chain of insulin. In one preferred embodiment, the B chain is the naturally occurring amino acid sequence of the B chain of insulin. It is preferred that the amino acid sequence of the ACB-proinsulin molecule of these species be the naturally occurring amino acid sequence of the A-chain and the naturally occurring sequence of the B-chain. Other embodiments of the invention may be directed to functional analogs of the proinsulin molecule derived from the aforementioned species.

Thus, in one preferred embodiment, the A chain is a variant or functional derivative of the A chain of insulin. In another preferred embodiment, the B chain is a variant or functional derivative of the B chain of insulin. In another preferred embodiment, the A chain is a variant or functional derivative of the A chain of insulin and the B chain is a variant or functional derivative of the B chain of insulin.

Natural amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

As used herein, the term "non-natural amino acid" or "unnatural amino acid" includes alpha and alpha-disubstituted amino acids, N-alkyl amino acids, lactic acid, halide derivatives of natural amino acids such as trifluorotyrosine, p-Cl-phenylalanine, p-F-phenylalanine, p-Br-phenylalanine, p-NO$_2$-phenylalanine, phenylglycine, sarcosine, penicillamine, D-2-methyltryptophan, phosphoserine, phosphothreonine, phosphotyrosine, p-I-phenylalanine, L-allyl-glycine, β-alanine, β-aspartic acid, β-cyclohexylalanine, citrulline, homoserine, homocysteine, pyroglutamic acid, L-α-amino butyric acid, L-γ-amino butyric acid, L-α-amino isobutyric acid, α-cyclohexylglycine, diaminobutyric acid, diaminopimelic acid, N-ε-dinitrophenyl-lysine, L-1-naphthylalanine, L-2-naphthylalanine, 3-(2-pyridyl)-L-alanine, 3-(3-pyridyl)-L-alanine, 3-(4-pyridyl)-L-alanine, N-ε-methyl-lysine, N,N-ε-dimethyl-lysine, N,N,N-ε-trimethyl-lysine, 3-mercaptopropionic acid, L-ε-amino caproic acid, 7-amino heptanoic acid, 6-amino hexanoic acid L-methionine sulfone, ornithine, L-norleucine, L-norvaline, p-nitro-L-phenylalanine, L-hydroxyproline, γ-glutamic acid, γ-amino butyric acid L-thioproline, methyl derivatives of phenylalanine (Phe) such as 4-methyl-Phe, pentamethyl-Phe, L-Phe (4-amino), L-Tyr (methyl), L-Phe (4-isopropyl), L-Tic (1,2,3,4tetrahydroiso-quinoline-3-carboxyl acid), L-diaminopropionic acid and L-Phe (4-benzyl).

Advantageously, the introduction of one or more unnatural amino acids leads to an increase in the enzymatic stability of the peptides.

The insulin analogues of the present invention may comprise amino acids in the L or D form, i.e. one or more residues, preferably all the residues, may be in the L or D form.

In the peptides of the invention, each of $X_1$ and $X_3$ is independently a basic amino acid. Having a basic amino acid present in the connecting peptide allows the peptide to be cleaved with trypsin and carboxypeptidase.

In the peptides of the invention, each $X_2$ is independently a natural or unnatural amino acid. Where $X_2$ is a cysteine residue, the skilled person would appreciate the need for protection to avoid unwanted S-S bond formation during subsequent oxidative folding. Suitable cysteine protecting groups will be familiar to the skilled person and include Acm and Trt.

In one preferred embodiment, $X_2$ is other than cysteine.

In one preferred embodiment, each $X_2$ is independently selected from a basic amino acid, Gly, β-Ala, Pro, Hyp, a pseudoproline, an acidic amino acid and a hydrophilic amino acid.

In one preferred embodiment, $X_2$ is a pseudoproline. Pseudoprolines are artificially created dipeptides that minimize aggregation during FMOC solid phase synthesis of peptides. Pseudoprolines consist of serine- (Oxa) or threonine-derived oxazolidines [Oxa(5-Me)] and Cysteine-derived thiazolidines (THz) with Proline-like ring structures (see below).

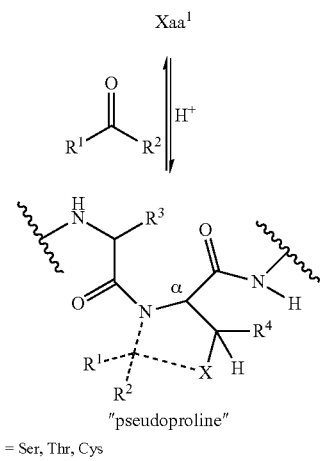

Xaa$^1$ = Ser, Thr, Cys

Due to the preference for a cis-amide bond with the preceding residue of C2-substituted pseudoprolines, their incorporation results in a kink conformation of the peptide backbone, thereby preventing peptide aggregation, self-association, or β-structure formation. Hence, pseudoprolines fulfil two functions simultaneously: firstly, they serve as temporary side-chain protection for Ser, Thr, and Cys, and secondly they act as solubilizing building blocks to increase solvation and coupling rates during peptide synthesis and in subsequent chain assembly.

Pseudoprolines are obtained by reacting the free amino acids with aldehydes or ketones. Pseudoproline dipeptides can be introduced in the same manner as other amino acid derivatives. Preferably the pseudoproline is derived from a Ser-X, Thr-X or CysX group, where X is a natural or unnatural amino acid. The routine use of pseudoproline (oxazolidine) dipeptides in the FMOC solid phase peptide synthesis (SPPS) of serine- and threonine-containing peptides leads to significant improvements in quality and yield of crude products. Once the peptide is deprotected, the pseuoproline becomes a conventional dipeptide of the form X-Ser, X-Thr or X-Cys, wherein X is a natural or unnatural amino acid.

In one preferred embodiment, $X_2$ is Hyp. As used herein, Hyp refers to (2S,4R)-4-hydroxyproline, or L-hydroxyproline, which is a non-proteinogenic amino acid having the following structure:

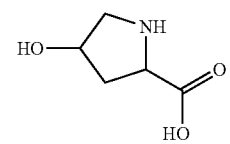

In one preferred embodiment, $X_2$ is an acidic or hydrophilic acid. Asp and Glu are examples of acidic amino acids, whereas Ser, Cys, Asn, Gln and Thr are examples of hydrophilic amino acids include. Preferably, the acidic or hydrophilic amino acid is selected from Ser, Asp and Glu.

In one preferred embodiment, $X_2$ is a basic amino acid. More preferably, the basic amino acid is selected from Lys, Arg, Orn and His. Even more preferably, the basic amino acid is Arg.

In one highly preferred embodiment, each $X_2$ is independently selected from Gly and Arg. More preferably, $X_2$ is Gly.

In one preferred embodiment, $X_1$ and $X_3$ are both Arg.
In one preferred embodiment, p and q are both 1.
In another preferred embodiment, p and q are both 2.
In one preferred embodiment, n is 1 or 2.
In one particularly preferred embodiment, n is 1.
In one particularly preferred embodiment, p and q are both 2, and n is 1.
In one preferred embodiment, n and q are both 0 and p is 1, i.e. the A chain and the B chain are separated by a single basic amino acid. For this embodiment, preferably $X_1$ is Arg or Lys, more preferably, Arg.
In another preferred embodiment, $X_1$ and $X_3$ are both Arg, and p and q are both 2.
In another preferred embodiment, $X_2$ is Gly and n is 1.
In one particularly preferred embodiment, the A chain and the B chain are linked by the peptide RRGRR, i.e. C is a peptide wherein $X_1$ is Arg, $X_2$ is Gly, $X_3$ is Arg, p and q are both 2, and n is 1.
In one preferred embodiment, A is the A chain of native insulin, preferably human insulin, or a variant thereof, wherein: (a) one or more amino acid residues are substituted by a naturally or non-naturally occurring amino acid residue, (b) the order of two or more amino acid residues is reversed, (c) one, two or three amino acids are deleted, (d) a spacer group is present between any two amino acid residues, (e) one or more amino acid residues are in peptoid form, (f) the (N—C—C) backbone of one or more amino acid residues of the peptide has been modified, (g) one or more additional amino acids are present at the N-terminus and/or the C-terminus, or any of (a)-(g) in combination.
In one preferred embodiment, one to five amino acids of the native A chain are substituted, preferably, one to four, more preferably one to three, even more preferably, one or two amino acids. In one preferred embodiment, a single amino acid is substituted.
In one highly preferred embodiment, the A-chain comprises amino acids 1 to 21 of human insulin counting from the N-terminal end of the A chain.
In one highly preferred embodiment, the A-chain consists of amino acids 1 to 21 of human insulin counting from the N-terminal end of the A chain.
In another highly preferred embodiment, the A-chain comprises amino acids 1 to 20 of human insulin counting from the N-terminal end of the A chain.
In another highly preferred embodiment, the A-chain consists of amino acids 1 to 20 of human insulin counting from the N-terminal end of the A chain.
In one preferred embodiment, B is the B chain of native insulin, preferably human insulin, or a variant thereof, wherein: (a) one or more amino acid residues are substituted by a naturally or non-naturally occurring amino acid residue, (b) the order of two or more amino acid residues is reversed, (c) one, two or three amino acids are deleted, (d) a spacer group is present between any two amino acid residues, (e) one or more amino acid residues are in peptoid form, (f) the (N—C—C) backbone of one or more amino acid residues of the peptide has been modified, (g) one or more additional amino acids are present at the N-terminus and/or the C-terminus, or any of (a)-(g) in combination.
In one preferred embodiment, one to five amino acids of the native B chain are substituted, preferably, one to four, more preferably one to three, even more preferably, one or two amino acids. In one preferred embodiment, a single amino acid is substituted.
In one preferred embodiment, the B-chain comprises amino acids 1 to 29 of human insulin counting from the N-terminal end of the A chain.

In one preferred embodiment, the B-chain consists of amino acids 1 to 29 of human insulin counting from the N-terminal end of the A chain.
In one preferred embodiment, the peptide of the invention is extended by one or more amino acids at the amino and/or the carboxyl terminus. For example, in one highly preferred embodiment, the peptide comprises two additional amino acids at its C-terminus, for example, Arg-Arg.
In one preferred embodiment, the B-chain of insulin further comprises up to 20 additional natural or unnatural amino acids at the C-terminal end. Preferably, the B-chain further comprises from 1 to 10, or more preferably from 1 to 5 additional natural or unnatural amino acids at the C-terminal end. In one highly preferred embodiment, the B-chain further comprises 1, 2 or 3 additional natural or unnatural amino acids at the C-terminal end. More preferably still, the B-chain further comprises 1, 2 or 3 additional natural amino acids at the C-terminal end.
In one preferred embodiment, the peptide comprises a single amino acid change from the native sequence. Preferably, the single amino acid change is at the position A21, B9, B10, B12, B16, B17, B20, B25, B26, B27, B28 or B30, where A denotes the A chain of insulin, and B denotes the B chain of insulin.
Preferably, the single amino acid substitution is selected from the following: Gly A21, Glu A21, hSer A21, Thr B10, Asp B25, Ser A21, Leu A21, Gly A22, Asp B10, His B25, Ala A21, Met A21, Ala A22, Arg B10, Glu B26, His A21, Tyr A21, Asp B9, Ile B12, Glu B27, Asp A21, Val A21, Asn B9, His B16, Asp B28, Thr A21, Ile A21, His B9, Gln B17, Ala B30, Gln A21, Trp A21, Glu B10, Gln B20, des-B30, Thr30-NH$_2$ and Ala30-NH$_2$.
In one preferred embodiment, the peptide comprises two amino acids change from the native sequence. Preferably, the two amino acids are at positions: A21 and B10, A21 and B10, A21 and B27, B27 and B16, B5 and B10, B12 and B13, B14 and B17, B28 and B29, A121 and B27, B10 and B30, B29 and B30, B12 and B30, B10 and B2, B10 and B28, B10 and A13, B27 and A13, B27 and A21, B27 and B1, B27 and B9, or A21 and B30.
Preferably, the two amino acid substitutions are selected from the following:
Ser A21 and Asp B10
Asp A21 and Lys B27
Thr A21 and Asp B10
Gly A21 and Arg B27
Ala A21 and Asp B10
Asp B5 and Asn B10
Thr A21 and Thr B10
Glu B12 and Gln B13
Ala A21 and Thr B10
Ser B14 and Asp B17
His A21 and Thr B10
Ser A21 and Arg B27
His A21 and Asp B10
Thr A21 and Arg B27
Asp A21 and Asp B10
Ala A21 and Arg B27
Gly A21 and Thr B10
Gly A21 and Asp B10
His A21 and Lys B27
Glu B27 and Glu B16
Ser A21 and Thr B10
Lys B28 and Pro B29
Asp A21 and Thr B10
His A21 and Arg B27
Gly A21 and Arg B10

Asp A21 and Arg B27
Ser A21 and Arg B10
Glu B12 and des B30
Thr A21 and Arg B10
Gly A21 and Lys B27
Gly A21 and Ala B30
Ser A21 and Lys B27
Ser A21 and Ala B30
Thr A21 and Lys B27
Thr A21 and Ala B30
Ala A21 and Lys B27
Ala A21 and Ala B30
des B29 and des B30
hSer A21 and Ala B30
Asp B10 and Ser B2
Ala A21 and Arg B10
Asp B10 and Asp B28
His A21 and Arg B10
Glu B10 and Glu A13
Asp A21 and Arg B10
Glu B27 and Ser A13
Asp B10 and des-B30
Glu B27 and Asp A21
Thr B10 and des-B30
Glu B27 and Glu B1
Arg B10 and des-B30
Glu B27 and Asp B9

In one preferred embodiment, the peptide comprises three amino acid changes from the native sequence. Preferably, the three amino acid changes are selected from the following:

Gly A21+Lys B27+Gln A17
Ser A21+Lys B27+Gln A17
Thr A21+Lys B27+Gln A17
Ala A21+Lys B27+Gln A17
His A21+Lys B27+Gln A17
Asp A21+Lys B27+Gln A17
Gly A21+Lys B27+Gln B13
Ser A21+Lys B27+Gln B13
Thr A21+Lys B27+Gln B13
Ala A21+Lys B27+Gln B13
His A21+Lys B27+Gln B13
Asp A21+Lys B27+Gln B13
Gly A21+Arg B27+Gln A17
Ser A21+Arg B27+Gln A17
Thr A21+Arg B27+Gln A17
Ala A21+Arg B27+Gln A17
His A21+Arg B27+Gln A17
Asp A21+Arg B27+Gln A17
Gly A21+Arg B27+Gln B13
Ser A21+Arg B27+Gln B13
Thr A21+Arg B27+Gln B13
Ala A21+Arg B27+Gln B13
His A21+Arg B27+Gln B13
Asp A21+Arg B27+Gln B13
Asp B10+His A8+His B25
Glu B10+Glu A3+Glu B22
Glu B27+Ser B5+Asp B5
Glu B27+His A5+Asp B9
Glu B27+Asp A21+Asp B9
des B28+des B29+des B30
Gly A21+Asp B10+Ala B30
Ser A21+Asp B10+Ala B30
Thr A21+Asp B10+Ala B30
Ala A21+Asp B10+Ala B30
His A21+Asp B10+Ala B30
Asp A21+Asp B10+Ala B30
Gly A21+Thr B10+Ala B30
Ser A21+Thr B10+Ala B30
Thr A21+Thr B10+Ala B30
Ala A21+Thr B10+Ala B30
His A21+Thr B10+Ala B30
Asp A21+Thr B10+Ala B30
Gly A21+Arg B10+Ala B30
Ser A21+Arg B10+Ala B30
Thr A21+Arg B10+Ala B30
Ala A21+Arg B10+Ala B30
His A21+Arg B10+Ala B30
Asp A21+Arg B10+Ala B30
Gly A21+Asp B10+des B30
Ser A21+Asp B10+des B30
Thr A21+Asp B10+des B30
Ala A21+Asp B10+des B30
His A21+Asp B10+des B30
Asp A21+Asp B10+des B30
Gly A21+Thr B10+des B30
Ser A21+Thr B10+des B30
Thr A21+Thr B10+des B30
Ala A21+Thr B10+des B30
His A21+Thr B10+des B30
Asp A21+Thr B10+des B30
Gly A21+Arg B10+des B30
Ser A21+Arg B10+des B30
Thr A21+Arg B10+des B30
Ala A21+Arg B10+des B30
His A21+Arg B10+des B30
Asp A21+Arg B10+des B30
Thr B10+Glu B28+Pro B29
Arg B10+Glu B28+Pro B29
Asp B10+Lys B28+Pro B29
Thr B10+Lys B28+Pro B29
Arg B10+Lys B28+Pro B29
Gly A21+Glu B28+Pro B29
Ser A21+Glu B28+Pro B29
Thr A21+Glu B28+Pro B29
Ala A21+Lys B28+Pro B29
His A21+Lys B28+Pro B29
Glu B28+Pro B29+Ala B30
Glu B28+Pro B29+des B30
Asp A21+Lys B28+ProB29
Lys B28+Pro B29+Ala B30
Lys B28+Pro B29+des B30
Arg B27+Gly A21+Thr B30NH$_2$ In one preferred embodiment, the peptide comprises four amino acid changes from the native sequence. Preferably, the four amino acid changes are selected from the following:

Ser A21+Arg B27+Gln A17+Gln B13
Thr A21+Arg B27+Gln A17+Gln B13
Ala A21+Arg B27+Gln A17+Gln B13
Asp A21+Arg B27+Gln A17+Gln B13
His A21+Arg B27+Gln A17+Gln B13
Glu B10+His A8+His B4+His B27
Gly A21+Lys B27+Gln A17+Gln B13
Ser A21+Lys B27+Gln A17+Gln B13
Thr A21+Lys B27+Gln A17+Gln B13
Ala A21+Lys B27+Gln A17+Gln B13
Asp A21+Lys B27+Gln A17+Gln B13
His A21+Lys B27+Gln A17+Gln B13
Gly A21+Arg B27+Gln A17+Gln B13
des B27+des B28+des B29+des B30
Gly A21+Asp B10+Glu B28+Pro B29
Ser A21+Asp B10+Glu B28+Pro B29
Thr A21+Asp B10+Glu B28+Pro B29
Ala A21+Asp B10+Glu B28+Pro B29

His A21+Asp B10+Glu B28+Pro B29
Asp A21+Asp B10+Glu B28+Pro B29
Gly A21+Thr B10+Glu B28+Pro B29
Ser A21+Thr B10+Glu B28+Pro B29
Thr A21+Thr B10+Glu B28+Pro B29
Ala A21+Thr B10+Glu B28+Pro B29
His A21+Thr B10+Glu B28+Pro B29
Asp A21+Thr E10+Glu B28+Pro B29
Ala A21+Arg B10+Glu B28+Pro B29
Ala A21+Asp B10+Lys B28+Pro B29
His A21+Asp B10+Lys B28+Pro B29
Asp A21+Asp B10+Lys B28+Pro B29
Gly A21+Arg B10+Glu B28+Pro B29
Ser A21+Arg B10+Glu B28+Pro B29
Thr A21+Arg B10+Glu B28+Pro B29
Gly A21+Thr B10+Lys B28+Pro B29
Ser A21+Thr B10+Lys B28+Pro B29
His A21+Arg B10+Glu B28+Pro B29
Asp A21+Arg B10+Glu B28+Pro B29
Gly A21+Asp B10+Lys B28+Pro B29
Ser A21+Asp B10+Lys B29+Pro B29
Thr A21+Asp B10+Lys B28+Pro B29
Ser A21+Arg B10+Lys B28+Pro B29
Thr A21+Arg B10+Lys B28+Pro B29
Ala A21+Arg B10+Lys B28+Pro B29
His A21+Arg B10+Lys B28+Pro B29
Asp A21+Arg B10+Lys B28+Pro B29
Gly A21+Glu B28+Pro B29+Ala B30
Ser A21+Glu B28+Pro B29+Ala B30
Thr A21+Lys B28+Pro B29+Ala B30
Ala A21+Lys B28+Pro B29+Ala B30
His A21+Lys B28+Pro B29+Ala B30
Asp A21+Lys B28+Pro B29+Ala B30
Thr A21+Thr B10+Lys B28+Pro B29
Ala A21+Thr B10+Lys B28+Pro B29
His A21+Thr B10+Lys B28+Pro B29
Asp A21+Thr B10+Lys B28+Pro B29
Gly A21+Arg B10+Lys B28+Pro B29
Gly A21+Glu B28+Pro B29+des B30
Ser A21+Glu B28+Pro B29+des B30
Thr A21+Glu B28+Pro B29+des B30
Ala A21+Glu B28+Pro B29+des B30
His A21+Glu B28+Pro B29+des B30
Thr B10+Glu B28+Pro B29+des B30
Arg B10+Glu B28+Pro B29+des B30
Asp B10+Lys B28+Pro B29+des B30
Thr B10+Lys B28+Pro B29+des B30
Arg B10+Lys B28+Pro B29+des B30
des B27+des B29+des B29+des B30
Asp A21+Glu B28+Pro B29+des B30
Gly A21+Lys B28+Pro B29+des B30
Ser A21+Lys B28+Pro B29+des B30
Thr A21+Lys B28+Pro B29+des B30
Ala A21+Lys B28+Pro B29+des B30
His A21+Lys B28+Pro B29+des B30
Asp A21+Lys B28+Pro B29+des B30
Asp B10+Glu B28+Pro B29+Ala B30
Thr B10+Glu B28+Pro B29+Ala B30
Arg B10+Glu B28+Pro B29+Ala B30
Asp B10+Lys B28+Pro B29+Ala B30
Thr A21+Glu B28+Pro B29+Ala B30
His A21+Glu B28+Pro B29+Ala B30
Asp A21+Glu B28+Pro B29+Ala B30
Gly A21+Lys B28+Pro B29+Ala B30
Ser A21+Lys B28+Pro B29+Ala B30
Thr B10+Lys B28+Pro B29+Ala B30
Arg B10+Lys B28+Pro B29+Ala B30
Asp B10+Glu B28+Pro B29+des B30

In one preferred embodiment, the peptide comprises five amino acid changes from the native sequence. Preferably, the five amino acid changes are at the following positions: B26, B27, B28, B29 and B30, for example, des B26+des B27+des B28+des B29+des B30.

In one preferred embodiment, C is a peptide of the sequence shown in SEQ ID NO:1,

[SEQ ID NO: 1]
RRGRR

In one preferred embodiment, A comprises a peptide of the sequence shown in SEQ ID NO:2,

[SEQ ID NO: 2]
$^1$GIVEQCCTSICSLYQLENYCG$^{21}$ wherein each amino acid is unprotected, or optionally protected, for example, where the amino acid side chain contains a functional group. Preferred protecting groups include acid cleavable protecting groups such as $^t$Bu, Acm, O'Bu, Trt, Mmt, Mtt and Pbf.

In a more preferred embodiment, A consists of a peptide of SEQ ID NO:2, wherein each amino acid is optionally protected.

In another preferred embodiment, A comprises a peptide of the sequence shown in SEQ ID NO:8,

[SEQ ID NO: 8]
$^1$GIVEQCCTSICSLYQLENYCN$^{21}$ wherein each amino acid is unprotected, or optionally protected, for example, where the amino acid side chain contains a functional group. Preferred protecting groups include acid cleavable protecting groups such as $^t$Bu, Acm, O'Bu, Trt, Mmt, Mtt and Pbf.

In a more preferred embodiment, A consists of a peptide of SEQ ID NO:8, wherein each amino acid is optionally protected.

In one preferred embodiment, B comprises a peptide of sequence shown in SEQ ID NO:3,

[SEQ ID NO: 3]
$^1$FVNQHLCGSHLVEALYLVCGERGFFYTPKT$^{30}$ wherein each amino acid is unprotected, or optionally protected, for example, where the amino acid side chain contains a functional group. Preferred protecting groups include acid cleavable protecting groups such as $^t$Bu, Acm, O'Bu, Trt, Mmt, Mtt and Pbf.

In a more preferred embodiment, B consists of a peptide of SEQ ID NO:3, wherein each amino acid is optionally protected.

In one preferred embodiment, the polypeptide compound is of SEQ ID NO:4:

SEQ ID NO: 4
$^1$GIVEQCCTSICSLYQLENYCGRRGRRFVNQHLCGS

HLVEALYLVCGERGFFYTPKT$^{56}$ wherein each amino acid is unprotected, or optionally protected, for example, where the amino acid side chain contains a functional group. Preferred protecting groups include acid cleavable protecting groups such as $^t$Bu, Acm, O'Bu, Trt, Mmt, Mtt and Pbf.

In one preferred embodiment, the polypeptide compound is selected from SEQ ID NOS: 4-7,

SEQ ID NO: 4
$^1$GIVEQCCTSICSLYQLENYCGRRGRRFVNQHLCGS

HLVEALYLVCGERGFFYTPKT$^{56}$

SEQ ID NO: 5
$^1$GIVEQCCTSICSLYQLENY<u>C</u>GRRGRRFVNQHLCGS

HLVEALYLV<u>C</u>GERGFFYTPKT$^{56}$

SEQ ID NO: 6
$^1$GIVEQ<u>C</u>CTSI<u>C</u>SLYQLENYCGRRGRRFVNQHLCGS

HLVEALYLVCGERGFFYTPKT$^{56}$

SEQ ID NO: 7
$^1$GIVEQC<u>C</u>TSICSLYQLENYCGRRGRRFVNQHL<u>C</u>GS

HLVEALYLVCGERGFFYTPKT$^{56}$ wherein in SEQ ID NOS: 4-7, <u>C</u> denotes a cysteine protected with a protecting group and C denotes an unprotected cysteine.

In one preferred embodiment, the cysteine protecting group is Acm or Trt.

In one preferred embodiment, the polypeptide compound is of formula I.1 (SEQ ID NO: 7)

(I.1)

wherein PG$_1$ and PG$_2$ are each independently a cysteine protecting group, and C—SH represents an unprotected cysteine. Preferably, PG$_1$ and PG$_2$ are each independently Acm or Trt.

Suitable protecting groups for amino acids will be familiar to the skilled person. Examples may be found in T.W. Greene & P.G.M. Wuts, Protective Groups in Organic Synthesis (2nd edition) J. Wiley & Sons, 1991; and P. J. Kocienski, Protecting Groups, Georg Thieme Verlag, 1994.

As used herein, Acm refers to the S-acetomidomethyl protecting group. Treatment of peptides containing S-Acm protecting group with iodine results in simultaneous removal of the sulfhydryl protecting group and disulfide formation.

As used herein, Trt refers to the triphenylmethyl protecting group. Trt protecting groups are acid labile and can be removed under acidic conditions (e.g. treatment with TFA).

In a more preferred embodiment, the polypeptide compound is of formula (I.1a) (SEQ ID NO: 9):

(I.1a)

wherein C—SH represents an unprotected cysteine

Processes for Preparing Proinsulin Derivatives

The proinsulin derivatives of the invention can be prepared by traditional synthetic methods (e.g. solid phase methods), or by recombinant methods.

In one preferred embodiment, the invention relates to a process for preparing a polypeptide compound as defined above using solid-phase peptide synthesis. The accompanying examples section describes such a synthesis in more detail.

Syntheses can be performed using the Fmoc/tBu-protection scheme using the 2-chlorotrityl resin as the solid support. For the protection of the Cys-residues, Trt or the Trt/Acm protecting groups can be used.

In alternative embodiment, the peptide compounds of the invention can be prepared recombinantly by methods known in the art. For further details, see for example, the teachings of EP0518587A.

One aspect of the invention therefore relates to a DNA sequence encoding a peptide compound as defined above.

Another aspect of the invention relates to a recombinant DNA vector comprising a DNA sequence as described above.

Another aspect of the invention relates to a process for the recombinant preparation of a polypeptide compound as defined above, said method comprising the steps of:

(i) constructing a DNA sequence encoding a polypeptide compound as defined above, (ii) incorporating said DNA sequence into a suitable vector containing a promoter-operator region functional in a host cell, (iii) orienting said DNA sequence in said vector so as to achieve transcription and translation of said DNA sequence and further that said DNA sequence is under the transcriptional control of said promoter-operator region, (iv) transforming said host cell with said vector, (v) culturing said transformed host cell under conditions appropriate so as to induce transcription and translation of said gene, and (vi) recovering and purifying the polypeptide product encoded by said DNA sequence.

Another aspect of the invention relates to a process for preparing insulin or a derivative thereof, said method comprising the steps of:

(i) constructing a DNA sequence encoding a polypeptide compound as defined above;

(ii) incorporating said DNA sequence into a suitable vector containing a promoter-operator region functional in a host cell, (iii) orienting said DNA sequence in said vector so as to achieve transcription and translation of said DNA sequence and further that said DNA sequence is under the transcriptional control of said promoter-operator region, (iv) transforming said host cell with said vector, (v) culturing said transformed host cell under conditions appropriate so as to induce transcription and translation of said gene, and (vi) recovering and purifying the polypeptide product encoded by said DNA sequence.

(vii) cleaving said polypeptide product encoded by said gene to excise the C-peptide.

Process for Oxidative Folding of Proinsulin Derivatives and Intermediates Therein A further aspect of the invention relates to a process for preparing insulin, or a derivative thereof, said process comprising the steps of:

(i) preparing a polypeptide compound according to the invention, and (ii) cleaving said polypeptide to excise the C-peptide.

The folding of the obtained inverse "super mini" proinsulins described herein can be performed either in one step or in two steps. The removal of the C-peptide can be performed in a conventional manner by trypsin and/or carboxypeptidase B. The accompanying examples section describes the synthesis of an ACB-proinsulin derivative with the side-chains of the Cys residues protected either with 6 Trt, or 2 Acm and 4 Trt groups in the three possible combinations. Their folding efficiency was then compared and the nature of the resulting products analysed by HPLC.

The results demonstrated that A-C-B proinsulin peptides can be prepared in high purity and yield. The use of a two-step oxidation procedure was shown to be particularly effective. In this way, folded, single-chain insulin precursors can be transformed into bioactive two-chain insulin by the enzymatic removal of the chain-bridging C-peptide.

A further aspect of the invention relates to a process for preparing insulin, or a derivative thereof, said process comprising the steps of:

(i) preparing an A-C-B polypeptide, and (ii) cleaving said polypeptide to excise the C-peptide.

In a preferred embodiment, A and B are defined as for formula (I), and C is the connecting peptide of insulin, or a variant thereof. In another preferred embodiment, C is a peptide as defined in formula (I), i.e. $(X_1)_p\text{-}(X_2)_n\text{-}(X_3)_q$.

In one preferred embodiment, the cysteine residue in the 7-position of the A chain of insulin and the cysteine residue in the 7-position of the B chain of insulin are each protected with a protecting group.

In one preferred embodiment, the cysteine residues in the 6-,11- and 20-positions of the A chain are unprotected, and the cysteine residue in the 19-position of the B chain is unprotected.

In another preferred embodiment, the cysteine residues in the 6-,11- and 20-positions of the A chain and the 19-position of the B chain are unprotected, and the cysteine residue in the 7-position of the A chain and the 7-position of the B chain are each protected with a protecting group.

Preferably, the protecting group is Acm or Trt, more preferably Acm.

In one particularly preferred embodiment, the process comprises a stepwise oxidative folding of the peptide compound, said process comprising the steps of:

(i) oxidising a peptide as defined above to form a first intermediate;

(ii) oxidising said first intermediate to form a second intermediate;

(iii) cleaving said second intermediate to excise the C-peptide.

Preferably, the peptide is of formula I.1 or I.1a as defined above.

In one preferred embodiment, step (i), the first oxidation step, comprises treating the peptide with DMSO to form a first intermediate. The remaining protecting groups are then removed and the resulting intermediate is then subjected to a further (second) oxidation step to form a second intermediate. The protecting groups of the intermediate can be removed by any suitable method. Thus, incorporating orthogonal cysteine protecting groups in the starting peptide allows the oxidative folding process to be dictated in a preferential manner.

More preferably, step (i) comprises treatment with DMSO in Gly buffer, more preferably 20% DMSO in 0.1M Gly buffer. Preferably, the pH of the mixture is greater than 9, more preferably, greater than 10, more preferably still, about 10.5. Preferably, the oxidation takes place over a period of at least 4 hours, more preferably at least 8 hours, more preferably at least 21 hours, even more preferably, 1 day. Preferably, the reaction is carried out at room temperature.

In one preferred embodiment, step (ii), the second oxidation step, comprises treating the first intermediate with iodine in acetic acid/water.

Preferably, the second oxidation step is carried out using iodine in AcOH/water in a ratio of about 4:1. Preferably, the reaction takes place over a period of at least 30 minutes, more preferably, at least 1 hour. Preferably, the reaction is carried out at room temperature.

In one preferred embodiment, the cleavage step (iii) comprises treating the second intermediate with trypsin.

Preferably, the cleavage of the C peptide is carried out at room temperature. Preferably, the reaction is carried out using trypsin in tris-buffer. Preferably the pH is greater than 7.5, more preferably about 8. Preferably, the reaction is carried out over a period of about 5 minutes.

In one particularly preferred embodiment, the process of the invention is as shown below in Scheme 1:

Scheme 1: Two step oxidative folding

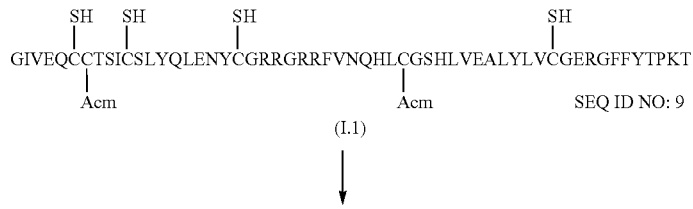

-continued

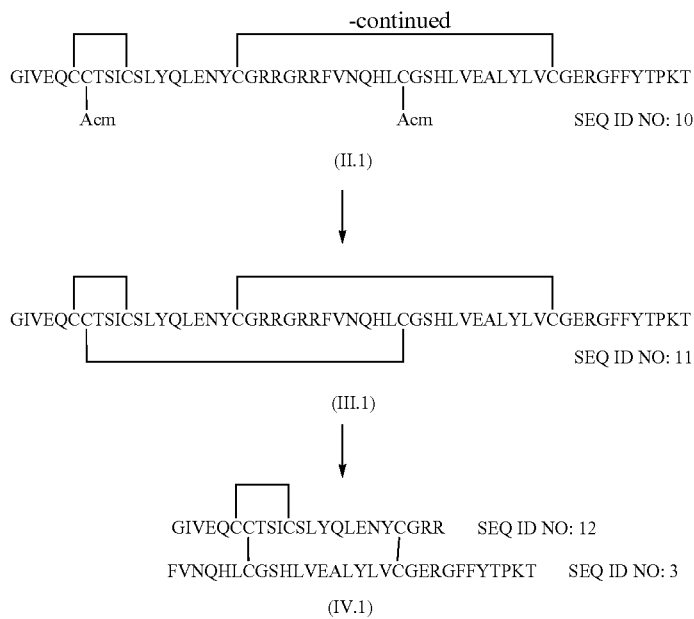

Another aspect of the invention relates to the use of a peptide compound as defined above in the preparation of insulin, or a derivative thereof.

Another aspect of the invention relates to intermediate polypeptide compounds in the oxidative folding process.

Thus, in one embodiment, the invention relates to a polypeptide of formula (I.1) (SEQ ID NO: 7):

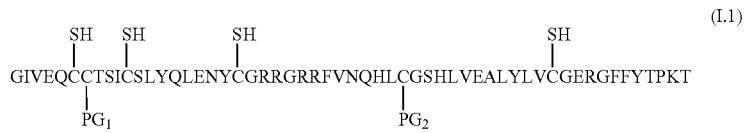

wherein $PG_1$ and $PG_2$ are each independently a cysteine protecting group, preferably Acm or Trt, more preferably Acm.

Thus, in one preferred embodiment, the invention relates to a polypeptide compound of formula (I.1a) (SEQ ID NO: 9):

In another preferred embodiment, the invention relates to a polypeptide of formula (II.1) (SEQ ID NO: 13):

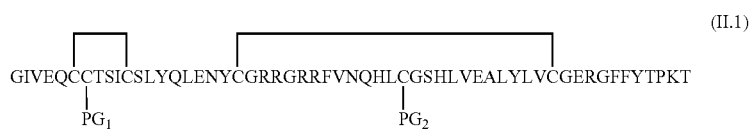

wherein $PG_1$ and $PG_2$ are each independently a cysteine protecting group, preferably Acm or Trt, more preferably Acm.

Thus, in one preferred embodiment, the invention relates to a peptide compound of formula (II.1a) (SEQ ID NO: 10):

(II.1a)

In another embodiment, the invention relates to a peptide compound of formula of formula (III.1) (SEQ ID NO: 11):

(III.1)

Peptides of formula I.1, I.1a, II.1 and II.1a are useful intermediates in the preparation of insulin.

Pharmaceutical Compositions One aspect of the invention relates to a pharmaceutical composition comprising a proinsulin derivative of the invention admixed with a pharmaceutically acceptable diluent, excipient or carrier, or a mixture thereof. Even though the proinsulin derivatives of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

For example, compounds of the invention can be admixed with conventional pharmaceutical carriers and excipients and used in the form of tablets, capsules, elixirs, suspensions, syrups, wafers and the like. The compositions comprising ACB-proinsulin compounds will typically contain from about 0.1 to 90% by weight of the active compound, and more generally from about 10 to 30%. The compositions may contain common carriers and excipients such as corn starch or gelatin, lactose, sucrose, microcrystalline cellulose, kaolin, mannitol, dicalcium phosphate, sodium chloride, and alginic acid.

Disintegrators commonly used in the formulations of this invention include croscarmellose, microcrystalline cellulose, corn starch, sodium starch, glycolate and alginic acid.

Examples of suitable excipients for the various different forms of pharmaceutical compositions described herein may be found in the "Handbook of Pharmaceutical Excipients, $2^{nd}$ Edition, (1994), Edited by A Wade and PJ Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Tablet binders that can be included are acacia, methyl cellulose, sodium carboxymethyl cellulose, polyvinylpyrrolidone (Povidone), hydroxypropyl methylcellulose, sucrose, starch and ethylcellulose.

Examples of suitable lubricants include sodium oleate, sodium stearate, magnesium stearate or other metallic stearates, sodium benzoate, sodium acetate, sodium chloride, stearic acid, silicone fluid, talc, waxes, oils and colloidal silica and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used. Suitable flavoring agents include peppermint, oil of wintergreen, cherry flavoring, or the like. It may be desirable to add a coloring agent to make the dosage form more attractive in appearance or to help identify the product.

For intravenous (IV) use, a water soluble form of compounds of the invention can be dissolved in one of the commonly used intravenous fluids and administered by infusion.

Such fluids, for example, physiological saline, Ringer's solution or 5% dextrose solution can be used.

For intramuscular preparations, a sterile formulation of a suitable soluble salt form of the compounds of the invention, for example the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of a suitable salt form of ACB-proinsulin, for example, the hydrochloride salt, formulated in a diluent such as distilled or deionized water, is particularly useful.

Alternatively, the unit dosage form of the compound can be solution of the compound, preferably in its salt form, in a suitable diluent in sterile hermetically sealed ampoules.

The concentration of the compound in the unit dosage may vary, e.g. from about 1% to about 50% depending on the particular form of the compound and its solubility and the dose desired by the physician.

Salts/Esters The proinsulin derivatives of the present invention can be present as salts or esters, in particular pharmaceutically acceptable salts or esters.

Pharmaceutically acceptable salts of the proinsulin derivatives of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of the proinsulin derivatives of the invention. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the proinsulin derivatives of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those analogues, and mixtures thereof. The terms used in the claims encompass these forms, provided said forms retain the appropriate functional activity (though not necessarily to the same degree).

The present invention also includes all suitable isotopic variations of the proinsulin derivatives or pharmaceutically acceptable salts thereof. An isotopic variation is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{13}N$, $^{17}O$, $^{18}O$, $^{31}P$, $^{32}P$, $^{35}S$, $^{18}F$ and $^{36}Cl$, respectively. Certain isotopic variations, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the analogues of the present invention and pharmaceutically acceptable salts thereof of this invention can generally be prepared by conventional procedures using appropriate isotopic variations of suitable reagents.

Solvates

The present invention also includes solvate forms of the compounds of the present invention. The terms used in the claims encompass these forms.

Polymorphs

The invention furthermore relates to compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes proinsulin derivatives of the present invention in prodrug form. Such prodrugs are generally analogues of the invention wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Therapeutic Use

Another aspect of the invention relates to proinsulin derivatives as described above for use as a medicament.

Another aspect of the invention relates to proinsulin derivatives as described above for use in treating or preventing diabetes, or treating or preventing hyperglycemia.

Preferably, the diabetes is type 2 diabetes mellitus.

Another aspect of the invention relates to proinsulin derivatives as described above in the preparation of a medicament for treating diabetes, or treating or preventing hyperglycemia.

As used herein the phrase "preparation of a medicament" includes the use of an analogue of the invention directly as the medicament in addition to its use in a screening programme for further therapeutic agents or in any stage of the manufacture of such a medicament.

Another aspect of the invention relates to a method of treating diabetes or treating or preventing hyperglycemia in a subject in need thereof, said method comprising administering to the subject a therapeutically effective amount of a single chain insulin analogue as described above.

Preferably, the method comprises administering to the organism an amount of ACB-proinsulin in a dose between about 10 and 1000 µg/kg. A more preferred dose is from about 10 to 100 µg/kg of active compound. A typical daily dose for an adult human is from about 0.5 to 100 mg.

In practicing this method, compounds of the invention can be administered in a single daily dose or in multiple doses per day. The treatment regime may require administration over extended periods of time. The amount per administered dose or the total amount administered will depend on such factors as the nature and severity of the disease, the age and general health of the patient and the tolerance of the patient to the compound.

A convenient method of practicing the treatment method is to administer the compounds of the invention via intravenous infusion. In this procedure a sterile formulation of a suitable soluble salt of the compound is incorporated in a physiological fluid, such as 5% dextrose solution, and the resulting solution is infused slowly IV. Alternatively, the piggy-back method of IV infusion can also be used.

The present invention is further described by way of the following non-limiting examples.

EXAMPLES

Abbreviations

Acm 5-acetomidomethyl
Boc t-butyloxycarbonyl
CTC chlorotrityl chloride
NMP N-methylpyrrolidone
DCM dichoromethane
TFA trifluoroacetic acid
RE rotary evaporator
DEE diethyl ether
DIC N,N'-diisopropylcarbodiimide
HOBt hydroxybenzotriazole
HOSu N-hydroxysuccinimide
Hyp (2S,4R)-4-hydroxyproline, or L-hydroxyproline
DMF dimethylformamide
EDAC 1-ethyl-3-(3-dimethylaminopropyl)carbodiimide
RT room temperature
DTT dithiothreitol
DMSO dimethylsulfoxide
MMt monomethoxytrityl
Trt trityl
DIPEA/DIEA N,N-diisopropylethylamine
Fmoc fluorenylmethyloxycarbonyl
MeOH methanol
AcOH acetic acid
TFE trifluoroethyl alcohol
Dde N-(1-(4,4-dimethyl-2,6-dioxocyclohexylidene)ethyl)
IPA isopropyl alcohol
TES triethylsilane Example 1

Solid-Phase Synthesis of A-Arg-Arg-Gly-Arg-Arg-B Proinsulin (ACB-Proinsulin) General procedure:

A1. Preparation of Loaded 2-Chlorotrityl Resins

2-Chlorotrityl chloride resin (CTC-Cl) (2 g; loading 1.6 mmol/g) from CBL-Patras, was placed in a 60 ml peptide synthesis reactor and swelled with 15 ml dichloromethane (DCM) for 15 min at 25° C. The resin was filtered and a solution of 1 mmol Fmoc-amino acid and 8 mmol diisopropylethylamine (DIEA) in 10 ml DCM was added. The mixture was stirred for 2 hours at 25° C. The remaining active sites of 2-CTC resin were neutralised by adding 1 ml of methanol (MeOH) and reacting for 1 hour. The resin was filtered and washed three times with 10 ml each of a mixture consisting of DCM/MeOH/DIPEA (85:10:5) and three times with NMP. After washing the resin was treated twice with 10 ml 25% by volume piperidine in NMP for 30 min. The resin was washed five times with 10 ml NMP. The resin was unswelled with 3 washes with 10 ml of isopropanol (IPA) and dried to constant weight. 70-95% mmol of the amino acid used was bound on the resin.

B. Solid-Phase Synthesis, a General Protocol

The solid-phase synthesis was performed at 24° C., with 1.0 g amino acid esterified to the CTC resin as described in Part A of Example 1. During the whole synthesis the following protocol was used.

B1. Swelling of the Resin

The resin was placed in a 20 ml plastic syringe equipped with a porous polypropylene frit and treated twice with 7 ml NMP, followed by filtration.

B2. Activation of the Amino Acid

The amino acid (3.0 equiv.) and 1-hydroxybenzotriazol (4.0 equiv.) was dissolved in a 10 ml vial with 2.5 times their volume in NMP and cooled to 0° C. DIC was then added (3.0 equiv.) and the mixture was stirred for 15 min.

B3. Coupling Reaction

The solution, which was prepared in B2 was then added to the B 1 reactor. The reactor was washed once with one volume of DCM and was added to the reactor which was stirred for 1-3 h at 25°–30° C. A Kaiser Test was performed to determine the completion of the reaction. If the coupling reaction was not completed after 3 h (positive Kaiser Test), the reaction mixture was filtered and recoupled with a fresh solution of activated amino acid. After completion of the coupling the reaction mixture was filtered and washed 6 times with NMP (5 volumes per wash).

B4. Removal of the Fmoc-Group

The resulting resin in B3 was filtered and then treated for 30 min with 5 ml of a solution, which contained 25% by volume of piperidine. The resin is washed 3×5 ml NMP.

B5. Elongation of the Peptide Chain

After the incorporation of each amino acid the steps B1-B5 were repeated until the desired peptide chain was formed.

The following Fmoc-amino acids were used for coupling of the individual amino acid or amino acid fragments: Fmoc-Gly-OH, Fmoc-Ala-OH, Fmoc-Val-OH, Fmoc-Ile-OH, Fmoc-Leu-OH, Fmoc-Phe-OH, Fmoc-Pro-OH, Fmoc-Asp(tBu)-OH, Fmoc-Glu(tBu)-OH, Fmoc-Lys(Boc)-OH, Fmoc-Ser(tBu)-OH, Fmoc-Thr(tBu)-OH, Fmoc-Tyr(tBu)-OH, Fmoc-Asn(Trt)-OH, Fmoc-Gln(Trt)-OH, Fmoc-Arg (Pbf)-OH, Fmoc-His(Trt)-OH, Fmoc-Cys(Trt)-OH and Fmoc-Cys(Acm)-OH; and the following Boc-amino acids: Boc-Gly-OH.

C. General Method for the Cleavage from the CTC-Resin of the Protected ACB Proinsulin Peptides and of their Protected Fragments, which Contain Fmoc- or Boc-Groups on their N-Terminus The resin-bound peptide or peptide segment which was produced as described above in B1-B5 was washed 4 times with 5 ml NMP, 3 times with 5 ml IPA and finally 5 times with 7 ml DCM to remove completely any residual NMP or other basic components. The resin was then cooled to 0° C., filtered from DCM and treated six times with a solution of 10 ml 1.0-1.5% TFA in DCM/TES (95:5) at 5° C.

The mixture was then stirred for 20 min at 0° C. and filtered. The resin was then washed three times with 10 ml DCM. Pyridine was then added to the filtrates (1.3 equiv. relative to TFA) to neutralize the TFA. The cleavage solution in DCM was then mixed with an equal volume of water. The resulting mixture was distilled at reduced pressure to remove DCM (350 Torr at 28° C.). The peptide or peptide fragment precipitated after the removal of DCM. The resulting peptide was washed with water and ether and dried at 30-35° C. under 15 Torr vacuum. Alternatively, DCM was removed in vacuum and the protected peptide was precipitated by the addition of diethyl ether.

Example 2

Deprotection of the Protected ACB-Proinsulin

General method: The protected ACB-proinsulin, obtained as described above in Example 1 (100 mg, 0.01 mmol) was treated with 10 ml TFA/TES/DTT/DCM (93:3:3:3) for 3 h at 5° C. and for 1 h at 22° C. The resulting solution was concentrated in vacuum and then the deprotected peptide was precipitated by the addition of diethylether and washed three times with 10 ml diethylether. The resulting solid was dried in vacuum (25° C., 15 Torr) until constant weight. Yield: 60 mg.

Example 3

One-step (random) oxidative folding of crude ACB-proinsulin (all Cys free) 10 mg of crude deprotected ACB-proinsulin (all Cys free) prepared as described in Example 2 was dissolved in 2 ml DMSO. To this solution a 0.1 M Gly buffer pH 10.5 was added (8 ml) and then solid Gnd.HCl, until a clear solution was obtained (1.9 g, about 2 M). The solution was left overnight at RT. During standing a small amount of precipitate was formed. HPLC-analysis of the supernatant (acidified with $CF_3CO_2H$ to pH 2) performed on a Waters Alliance 2695 system equipped with Waters 996 PDA detector, using a Purospher RP-8, 125×4 mm, 5 μm column (Merck) and a linear gradient of 10% B to 60% B, flow rate 1 ml/min, where A=1% TFA in water and B=1 TFA in acetonitrile, showed that a complicated mixture of trioxidized isomers was formed.

Example 4

Oxidative folding of [Cys(Acm)7, 33]-ACB-proinsulin 10 mg of crude deprotected [Cys(Acm)7,33]-ACB-proinsulin prepared as described in Example 2 was dissolved in 2 ml DMSO. To this solution a 0.1 M Gly buffer pH 10.5 was added (8 ml) and then solid Gnd.HCl, until a clear solution was obtained (1.9 g, about 2 M). The solution left overnight at RT. During standing a small amount of precipitate was formed. HPLC-analysis of the supernatant (acidified with $CF_3CO_2H$ to pH 2) performed as described in Example 4 above, showed that a major bis-oxidized product was formed, as confirmed by ESI-MS analysis on a Waters-Micromass ZQ4000 system. M calc. 6558.56 Da, M found 6558.36 Da.

Example 5

Purification of bis-oxidized [Cys(Acm)7, 33]-ACB-proinsulin

The solution of bis-oxidized [Cys(Acm)7, 33]-ACB-proinsulin, obtained as described in Example 4 above, was loaded after filtration through a 0.2 membrane syringe filter, in two portions on a Purospher RP-18 semi-preparative column, 10×250 mm (Merck); phase A=1% TFA in water, phase B=1% TFA in acetonitrile; isocratic 30% B for 5 min and then linear gradient from 30% B to 40% B in 30 min, flow rate 4 ml/min. Collected fractions of main product were frozen in liquid nitrogen and lyophilized. The purification yield was 30%.

Example 6

Determination of disulfide bond-pairing in bis-oxidized [Cys(Acm)7, 33]-ACB-proinsulin by *Staphylococcus Aureus* V8 protease fingerprinting 100 µg of purified bis-oxidized [Cys(Acm)7, 33]-ACB-proinsulin was dissolved in 150 uL of 0.1 M ammonium acetate, pH 4.0. 50 uL (5 µg) of a solution of *Staphylococcus Aureus* V8 protease (sequencing grade, commercially available from Sigma-Aldrich) in 0.1 M ammonium acetate was added and the digest incubated at 25° C. The progress of digestion was monitored by injecting 20 uL of the solution on a Purospher RP-8 HPLC column, using a gradient of 10% B to 60% B in 30 min. After 54 h the starting peptide was almost disappeared. ESI-MS analysis of the produced peaks confirmed the proper disulfide bond arrangement of the bis-oxidized- [Cys(Acm)7, 33]-ACB-proinsulin.

Example 7

Oxidation of bis-oxidized [Cys(Acm)7, 33]-ACB-proinsulin with iodine

Purified and lyophilized bis-oxidized [Cys(Acm)7, 33]-ACB-proinsulin (2 mg), obtained as described in Example 5 above was dissolved in a mixture of acetic acid/water 4:1 v/v (1 ml). This solution was then added over a period of 10 min in a solution of iodine (4 mg) in acetic acid/water 4:1 (1 ml), under shaking. After standing for 1 h at RT with occasional shaking, 2 drops of a 1 M solution of ascorbic acid in water was added to neutralize iodine excess (decoloration). This solution was then loaded in portions on a Purospher RP-8, 125X$_4$ mm HPLC column (Merck) and purified using a gradient of 10% B to 60% B in 30 min, flow rate 1 ml/min. Collected fractions of the main product were frozen in liquid nitrogen and lyophilized. Yield: 70%. ESI-MS: Mcalc. 6414.39 Da, Mfound 6413.83 Da.

Example 8

Trypsin cleavage of ACB-proinsulin

500 µg ACB-proinsulin was dissolved in 500 uL of 0.1 M Tris.HCl buffer pH 7.9, containing 2 M urea and 5 µg of trypsin (Sigma, slightly cloudy solution) at RT. The reaction was stopped after 5 min by acidification with trifluoroacetic acid (5 uL). The solution, after centrifugation, was loaded in 100 uL portions on a Purospher RP-8 column, as described in Example 7 and the main product was isolated. The product was analyzed by ESI-MS and corresponded to [GlyA21]-insulin plus 2 Arg residues (ESI-MS: Mcalc. 6062.97 Da, Mfound 6062.28 Da). After reduction of disulfide bonds with TCEP and LC-MS analysis of the two chains produced the product identified as the [GlyA21, ArgA22, ArgA23]-insulin.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

---

The invention claimed is:
1. A process for preparing insulin, or a derivative thereof, said process comprising the steps of:
  (a) preparing by solid phase synthesis a polypeptide compound of formula (I):

A-C-B    (I)

wherein:
    A is the A chain of insulin or a functional derivative or variant thereof;
    B is the B chain of insulin or a functional derivative or variant thereof;
    C is a peptide of the formula:

$(X_1)_p\text{-}(X_2)_n\text{-}(X_3)_q$ wherein:
    each $X_1$ and $X_3$ are both Arg;
    each $X_2$ is selected from the group consisting of a basic amino acid, Gly, β-Ala, Pro, Hyp, pseudoproline, and an acidic or hydrophilic amino acid;
    p is 2;
    q is 2; and
    n is 1 and
  (b) subjecting the polypeptide compound of formula (I) formed in step (a) to stepwise oxidative folding, wherein said stepwise oxidative folding comprises the steps of:
    (i) treating the polypeptide compound of formula (I) with DMSO to form a first intermediate;
    (ii) treating said first intermediate with iodine in acetic acid/water to form a second intermediate; and
    (iii) cleaving said second intermediate to excise the C-peptide.

2. The process according to claim 1 wherein the cysteine residue in the 7-position of the A chain of insulin and the cysteine residue in the 7-position of the B chain of insulin are each protected with a protecting group.

3. The process according to claim 2 wherein the protecting group is Acm or Trt.

4. The process according to claim 1 wherein step (b) (iii) comprises treating the second intermediate with trypsin.

5. The process according to claim 1 wherein $X_2$ is an acidic or hydrophilic amino acid selected from Ser, Asp and Glu.

6. The process according to claim 1 wherein $X_2$ is a basic amino acid selected from Lys, Arg, Orn and His.

7. The process according to claim 1 wherein each $X_2$ is independently selected from Gly and Arg.

8. The process according to claim 1 wherein A is the A chain of native insulin, or a variant thereof, wherein: (a) one or two amino acid residues are substituted by a naturally or non-naturally occurring amino acid residue, (b) the order of two amino acid residues is reversed, (c) one, two or three amino acids are deleted, (d) one additional amino acid is present at the N-terminus and/or the C-terminus, or any of (a)-(d) in combination.

9. The process according to claim 1 wherein B is the B chain of native insulin, or a variant thereof, wherein: (a) one to five amino acid residues are substituted by a naturally or non-naturally occurring amino acid residue, (b) the order of two amino acid residues is reversed, (c) one, two or three amino acids are deleted, (d) one additional amino acid is present at the N-terminus and/or the C-terminus, or any of (a)-(d) in combination.

10. The process according to claim 1 wherein C is a peptide of the sequence shown in SEQ ID NO:1,

[SEQ ID NO: 1]
RRGRR.

11. The process according to claim 1 wherein A comprises a peptide of the sequence shown in SEQ ID NO:2,

[SEQ ID NO: 2]
$^1$GIVEQCCTSICSLYQLENYCG$^{21}$, wherein each amino acid is unprotected, or optionally protected.

12. The process according to claim 1 wherein B comprises a peptide of the sequence shown in SEQ ID NO:3,

[SEQ ID NO: 3]
$^1$FVNQHLCGSHLVEALYLVCGERGFFYTPKT$^{30}$, wherein each amino acid is unprotected, or optionally protected.

13. The process according to claim 1, wherein the polypeptide compound is selected from SEQ ID NOS: 4-7,

SEQ ID NO:4
$^1$GIVEQCCTSICSLYQLENYCGRRGRRFVNQHLOGSHLVEALYLVOGERGFFYTPKT$^{56}$

SEQ ID NO:5
$^1$GIVEQCCTSICSLYQLENYC*GRRGRRFVNQHLOGSHLVEALYLVC*GERGFFYTPKT$^{56}$

SEQ ID NO:6
$^1$GIVEQC*CTSIC*SLYQLENYCGRRGRRFVNQHLCGSHLVEALYLVCGERGFFYTPKT$^{56}$

SEQ ID NO:7
$^1$GIVEQCC*TSICSLYQLENYCGRRGRRFVNQHLC*GSHLVEALYLVCGERGFFYTPKT$^{56}$ wherein in SEQ ID NOS: 4-7, C* denotes a cysteine protected with a protecting group and C denotes an unprotected cysteine.

14. The process according to claim 13 wherein the cysteine protecting group is Acm or Trt.

15. The process according to claim 1, wherein the polypeptide compound is of formula (I.1):

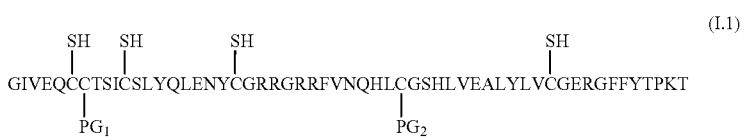

wherein PG$_1$ and PG$_2$ are each independently a cysteine protecting group.

16. A process according to claim 1 wherein the cysteine residues in the 6-, 11- and 20-positions of the A chain are unprotected, and the cysteine residue in the 19-position of the B chain is unprotected.

17. A process according to claim 1 wherein the polypeptide compound of formula (I) is of formula (I.1a):

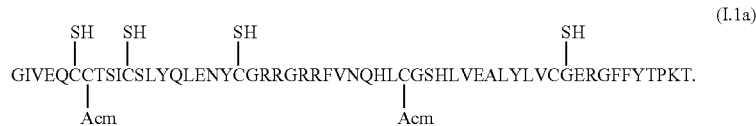

18. A process according to claim 1 wherein the first intermediate formed in step (b)(i) is of formula (II.1):

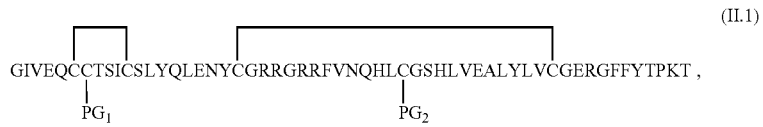

wherein PG$_1$ and PG$_2$ are each independently a cysteine protecting group.

19. A process according to claim 1 wherein the first intermediate formed in step (b)(i) is of formula (II.1a):

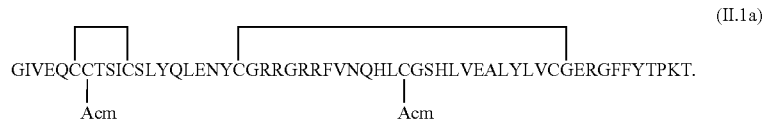

20. A process according to claim 1 wherein the second intermediate formed in step (b)(ii) is of formula (III.1):

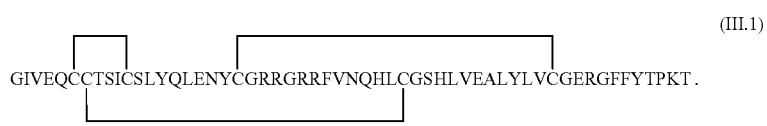

* * * * *

UNITED STATES PATENT AND TRADEMARK OFFICE
CERTIFICATE OF CORRECTION

PATENT NO. : 11,230,585 B2
APPLICATION NO. : 16/330154
DATED : January 25, 2022
INVENTOR(S) : Gatos et al.

It is certified that error appears in the above-identified patent and that said Letters Patent is hereby corrected as shown below:

In the Claims

Column 42, Claim 13, Lines 40 and 41, change:
SEQ ID NO:4
1GIVEQCCTSICSLYQLENYCGRRGRRFVNQHLOGSHLVEALYLVOGERGFFYTPKT56
To:
SEQ ID NO:4
1GIVEQCCTSICSLYQLENYCGRRGRRFVNQHLCGSHLVEALYLVCGERGFFYTPKT56

Column 42, Claim 13, Lines 43 and 44, change:
SEQ ID NO:5
1GIVEQCCTSICSLYQLENYC*GRRGRRFVNQHLOGSHLVEALYLVC*GERGFFYTPKT56
To:
SEQ ID NO:5
1GIVEQCCTSICSLYQLENYC*GRRGRRFVNQHLCGSHLVEALYLVC*GERGFFYTPKT56

Column 43, Claim 17, change:

```
     SH   SH      SH                            SH
     |    |       |                             |
  GIVEQCCTSICSLYQLENYCGRRGRRFVNQHLCGSHLVEALYLVCGERGFFYTPKT
         |                          |
         Acm              (I.1a)    Acm
```

To:

```
     SH   SH      SH                            SH
     |    |       |                             |
  GIVEQCCTSICSLYQLENYCGRRGRRFVNQHLCGSHLVEALYLVCGERGFFYTPKT
         |                          |
         Acm              (I.1a)    Acm
```

Signed and Sealed this
Tenth Day of May, 2022

*Katherine Kelly Vidal*

Katherine Kelly Vidal
*Director of the United States Patent and Trademark Office*

CERTIFICATE OF CORRECTION (continued)
U.S. Pat. No. 11,230,585 B2

Column 43, Claim 19, change:

GIVEQCCTSICSLYQLENYCGRRGRRFVNQHLCGSHLVEALYLVCGERGFFYTPKT
with disulfide bridges and Acm protecting groups on cysteines as shown To:

GIVEQCCTSICSLYQLENYCGRRGRRFVNQHLCGSHLVEALYLVCGERGFFYTPKT
with disulfide bridges and Acm protecting groups on cysteines as shown (II.1a)

SEQUENCE LISTING

```
<160> NUMBER OF SEQ ID NOS: 16

<210> SEQ ID NO 1
<211> LENGTH: 5
<212> TYPE: PRT
<213> ORGANISM: Artificial Sequence
<220> FEATURE:
<223> OTHER INFORMATION: Linker peptide

<400> SEQUENCE: 1

Arg Arg Gly Arg Arg
1               5

<210> SEQ ID NO 2
<211> LENGTH: 21
<212> TYPE: PRT
<213> ORGANISM: Artificial Sequence
<220> FEATURE:
<223> OTHER INFORMATION: Synthetic insulin chain

<400> SEQUENCE: 2

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 3
<211> LENGTH: 30
<212> TYPE: PRT
<213> ORGANISM: Homo sapiens

<400> SEQUENCE: 3
```

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 56
<212> TYPE: PRT
<213> ORGANISM: Artificial Sequence
<220> FEATURE:
<223> OTHER INFORMATION: Insulin analogue
<220> FEATURE:
<221> NAME/KEY: MISC_FEATURE
<222> LOCATION: (1)..(56)
<223> OTHER INFORMATION: amino acid may be unprotected or optionally
      protected

<400> SEQUENCE: 4

Gly Ile Val Glu Gln Cys Cys Thr Ser Ile Cys Ser Leu Tyr Gln Leu
1               5                   10                  15

Glu Asn Tyr Cys Gly Arg Arg Gly Arg Arg Phe Val Asn Gln His Leu
            20                  25                  30

Cys Gly Ser His Leu Val Glu Ala Leu Tyr Leu Val Cys Gly Glu Arg
        35                  40                  45

Gly Phe Phe Tyr Thr Pro Lys Thr
    50                  55

<210> SEQ ID NO 5
<211> LENGTH: 56
<212> TYPE: PRT
<213> ORGANISM: Artificial Sequence
<220> FEATURE:
<223> OTHER INFORMATION: Insulin analogue
<220> FEATURE:
<221> NAME/KEY: MISC_FEATURE
<222> LOCATION: (20)..(20)
<223> OTHER INFORMATION: cysteine protected with a protecting group
<220> FEATURE:
<221> NAME/KEY: MISC_FEATURE
<222> LOCATION: (45)..(45)
<223> OTHER INFORMATION: cysteine protected with a protecting group

<400> SEQUENCE: 5

Gly Ile Val Glu Gln Cys Cys Thr Ser Ile Cys Ser Leu Tyr Gln Leu
1               5                   10                  15

Glu Asn Tyr Cys Gly Arg Arg Gly Arg Arg Phe Val Asn Gln His Leu
            20                  25                  30

Cys Gly Ser His Leu Val Glu Ala Leu Tyr Leu Val Cys Gly Glu Arg
        35                  40                  45

Gly Phe Phe Tyr Thr Pro Lys Thr
    50                  55

<210> SEQ ID NO 6
<211> LENGTH: 56
<212> TYPE: PRT
<213> ORGANISM: Artificial Sequence
<220> FEATURE:
<223> OTHER INFORMATION: Insulin analogue
<220> FEATURE:
<221> NAME/KEY: MISC_FEATURE
<222> LOCATION: (6)..(6)
<223> OTHER INFORMATION: cysteine protected with a protecting group
<220> FEATURE:
<221> NAME/KEY: MISC_FEATURE
<222> LOCATION: (11)..(11)
<223> OTHER INFORMATION: cysteine protected with a protecting group
```

<400> SEQUENCE: 6

Gly Ile Val Glu Gln Cys Cys Thr Ser Ile Cys Ser Leu Tyr Gln Leu
1               5                   10                  15

Glu Asn Tyr Cys Gly Arg Arg Gly Arg Arg Phe Val Asn Gln His Leu
            20                  25                  30

Cys Gly Ser His Leu Val Glu Ala Leu Tyr Leu Val Cys Gly Glu Arg
        35                  40                  45

Gly Phe Phe Tyr Thr Pro Lys Thr
    50                  55

<210> SEQ ID NO 7
<211> LENGTH: 56
<212> TYPE: PRT
<213> ORGANISM: Artificial Sequence
<220> FEATURE:
<223> OTHER INFORMATION: Insulin analogue
<220> FEATURE:
<221> NAME/KEY: MISC_FEATURE
<222> LOCATION: (7)..(7)
<223> OTHER INFORMATION: cysteine protected with a protecting group
<220> FEATURE:
<221> NAME/KEY: MISC_FEATURE
<222> LOCATION: (33)..(33)
<223> OTHER INFORMATION: cysteine protected with a protecting group

<400> SEQUENCE: 7

Gly Ile Val Glu Gln Cys Cys Thr Ser Ile Cys Ser Leu Tyr Gln Leu
1               5                   10                  15

Glu Asn Tyr Cys Gly Arg Arg Gly Arg Arg Phe Val Asn Gln His Leu
            20                  25                  30

Cys Gly Ser His Leu Val Glu Ala Leu Tyr Leu Val Cys Gly Glu Arg
        35                  40                  45

Gly Phe Phe Tyr Thr Pro Lys Thr
    50                  55

<210> SEQ ID NO 8
<211> LENGTH: 21
<212> TYPE: PRT
<213> ORGANISM: Homo sapiens

<400> SEQUENCE: 8

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 9
<211> LENGTH: 56
<212> TYPE: PRT
<213> ORGANISM: Artificial Sequence
<220> FEATURE:
<223> OTHER INFORMATION: Insulin analogue
<220> FEATURE:
<221> NAME/KEY: MISC_FEATURE
<222> LOCATION: (7)..(7)
<223> OTHER INFORMATION: cysteine protected with a protecting group
     (Acm)
<220> FEATURE:
<221> NAME/KEY: MISC_FEATURE
<222> LOCATION: (33)..(33)
<223> OTHER INFORMATION: cysteine protected with a protecting group
     (Acm)

<400> SEQUENCE: 9

```
Gly Ile Val Glu Gln Cys Cys Thr Ser Ile Cys Ser Leu Tyr Gln Leu
1               5                   10                  15

Glu Asn Tyr Cys Gly Arg Arg Gly Arg Arg Phe Val Asn Gln His Leu
            20                  25                  30

Cys Gly Ser His Leu Val Glu Ala Leu Tyr Leu Val Cys Gly Glu Arg
        35                  40                  45

Gly Phe Phe Tyr Thr Pro Lys Thr
    50                  55
```

<210> SEQ ID NO 10
<211> LENGTH: 56
<212> TYPE: PRT
<213> ORGANISM: Artificial Sequence
<220> FEATURE:
<223> OTHER INFORMATION: Insulin analogue
<220> FEATURE:
<221> NAME/KEY: DISULFID
<222> LOCATION: (6)..(11)
<220> FEATURE:
<221> NAME/KEY: MISC_FEATURE
<222> LOCATION: (7)..(7)
<223> OTHER INFORMATION: cysteine protected with a protecting group
      (Acm)
<220> FEATURE:
<221> NAME/KEY: DISULFID
<222> LOCATION: (20)..(45)
<220> FEATURE:
<221> NAME/KEY: MISC_FEATURE
<222> LOCATION: (33)..(33)
<223> OTHER INFORMATION: cysteine protected with a protecting group
      (Acm)

<400> SEQUENCE: 10

```
Gly Ile Val Glu Gln Cys Cys Thr Ser Ile Cys Ser Leu Tyr Gln Leu
1               5                   10                  15

Glu Asn Tyr Cys Gly Arg Arg Gly Arg Arg Phe Val Asn Gln His Leu
            20                  25                  30

Cys Gly Ser His Leu Val Glu Ala Leu Tyr Leu Val Cys Gly Glu Arg
        35                  40                  45

Gly Phe Phe Tyr Thr Pro Lys Thr
    50                  55
```

<210> SEQ ID NO 11
<211> LENGTH: 56
<212> TYPE: PRT
<213> ORGANISM: Artificial Sequence
<220> FEATURE:
<223> OTHER INFORMATION: Insulin analogue
<220> FEATURE:
<221> NAME/KEY: DISULFID
<222> LOCATION: (6)..(11)
<220> FEATURE:
<221> NAME/KEY: DISULFID
<222> LOCATION: (7)..(33)
<220> FEATURE:
<221> NAME/KEY: DISULFID
<222> LOCATION: (20)..(45)

<400> SEQUENCE: 11

```
Gly Ile Val Glu Gln Cys Cys Thr Ser Ile Cys Ser Leu Tyr Gln Leu
1               5                   10                  15

Glu Asn Tyr Cys Gly Arg Arg Gly Arg Arg Phe Val Asn Gln His Leu
            20                  25                  30

Cys Gly Ser His Leu Val Glu Ala Leu Tyr Leu Val Cys Gly Glu Arg
        35                  40                  45

Gly Phe Phe Tyr Thr Pro Lys Thr
```

```
              50                  55

<210> SEQ ID NO 12
<211> LENGTH: 23
<212> TYPE: PRT
<213> ORGANISM: Artificial Sequence
<220> FEATURE:
<223> OTHER INFORMATION: Insulin analogue
<220> FEATURE:
<221> NAME/KEY: DISULFID
<222> LOCATION: (6)..(11)

<400> SEQUENCE: 12

Gly Ile Val Glu Gln Cys Cys Thr Ser Ile Cys Ser Leu Tyr Gln Leu
1               5                   10                  15

Glu Asn Tyr Cys Gly Arg Arg
            20

<210> SEQ ID NO 13
<211> LENGTH: 56
<212> TYPE: PRT
<213> ORGANISM: Artificial Sequence
<220> FEATURE:
<223> OTHER INFORMATION: Insulin analogue
<220> FEATURE:
<221> NAME/KEY: DISULFID
<222> LOCATION: (6)..(11)
<220> FEATURE:
<221> NAME/KEY: MISC_FEATURE
<222> LOCATION: (7)..(7)
<223> OTHER INFORMATION: cysteine protected with a protecting group
<220> FEATURE:
<221> NAME/KEY: DISULFID
<222> LOCATION: (20)..(45)
<220> FEATURE:
<221> NAME/KEY: MISC_FEATURE
<222> LOCATION: (33)..(33)
<223> OTHER INFORMATION: cysteine protected with a protecting group

<400> SEQUENCE: 13

Gly Ile Val Glu Gln Cys Cys Thr Ser Ile Cys Ser Leu Tyr Gln Leu
1               5                   10                  15

Glu Asn Tyr Cys Gly Arg Arg Gly Arg Arg Phe Val Asn Gln His Leu
            20                  25                  30

Cys Gly Ser His Leu Val Glu Ala Leu Tyr Leu Val Cys Gly Glu Arg
        35                  40                  45

Gly Phe Phe Tyr Thr Pro Lys Thr
    50                  55

<210> SEQ ID NO 14
<211> LENGTH: 56
<212> TYPE: PRT
<213> ORGANISM: Artificial Sequence
<220> FEATURE:
<223> OTHER INFORMATION: Insulin analogue

<400> SEQUENCE: 14

Gly Ile Val Glu Gln Cys Cys Thr Ser Ile Cys Ser Leu Tyr Gln Leu
1               5                   10                  15

Glu Asn Tyr Cys Gly Arg Arg Gly Arg Arg Phe Val Asn Gln His Leu
            20                  25                  30

Cys Gly Ser His Leu Val Glu Ala Leu Tyr Leu Val Cys Gly Glu Arg
        35                  40                  45

Gly Phe Phe Tyr Thr Pro Lys Thr
    50                  55
```

```
<210> SEQ ID NO 15
<211> LENGTH: 56
<212> TYPE: PRT
<213> ORGANISM: Artificial Sequence
<220> FEATURE:
<223> OTHER INFORMATION: Insulin analogue
<220> FEATURE:
<221> NAME/KEY: MISC_FEATURE
<222> LOCATION: (20)..(20)
<223> OTHER INFORMATION: cysteine protected with a protecting group
      (Acm)
<220> FEATURE:
<221> NAME/KEY: MISC_FEATURE
<222> LOCATION: (45)..(45)
<223> OTHER INFORMATION: cysteine protected with a protecting group
      (Acm)

<400> SEQUENCE: 15

Gly Ile Val Glu Gln Cys Cys Thr Ser Ile Cys Ser Leu Tyr Gln Leu
1               5                   10                  15

Glu Asn Tyr Cys Gly Arg Arg Gly Arg Arg Phe Val Asn Gln His Leu
            20                  25                  30

Cys Gly Ser His Leu Val Glu Ala Leu Tyr Leu Val Cys Gly Glu Arg
        35                  40                  45

Gly Phe Phe Tyr Thr Pro Lys Thr
    50                  55

<210> SEQ ID NO 16
<211> LENGTH: 56
<212> TYPE: PRT
<213> ORGANISM: Artificial Sequence
<220> FEATURE:
<223> OTHER INFORMATION: Insulin analogue
<220> FEATURE:
<221> NAME/KEY: MISC_FEATURE
<222> LOCATION: (6)..(6)
<223> OTHER INFORMATION: cysteine protected with a protecting group
      (Acm)
<220> FEATURE:
<221> NAME/KEY: MISC_FEATURE
<222> LOCATION: (11)..(11)
<223> OTHER INFORMATION: cysteine protected with a protecting group
      (Acm)

<400> SEQUENCE: 16

Gly Ile Val Glu Gln Cys Cys Thr Ser Ile Cys Ser Leu Tyr Gln Leu
1               5                   10                  15

Glu Asn Tyr Cys Gly Arg Arg Gly Arg Arg Phe Val Asn Gln His Leu
            20                  25                  30

Cys Gly Ser His Leu Val Glu Ala Leu Tyr Leu Val Cys Gly Glu Arg
        35                  40                  45

Gly Phe Phe Tyr Thr Pro Lys Thr
    50                  55
```